US010689615B2

(12) United States Patent
Morita et al.

(10) Patent No.: US 10,689,615 B2
(45) Date of Patent: Jun. 23, 2020

(54) TEMPERATURE-RESPONSIVE BASE MATERIAL, METHOD FOR PRODUCING SAME, AND METHOD FOR EVALUATING SAME

(71) Applicant: DAIKIN INDUSTRIES, LTD., Osaka-shi, Osaka (JP)

(72) Inventors: Masamichi Morita, Settsu (JP); Kouji Kubota, Settsu (JP); Yoshiko Koizumi, Settsu (JP); Hiroki Yamaguchi, Settsu (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 297 days.

(21) Appl. No.: 15/115,136

(22) PCT Filed: Jan. 29, 2015

(86) PCT No.: PCT/JP2015/052579
§ 371 (c)(1),
(2) Date: Jul. 28, 2016

(87) PCT Pub. No.: WO2015/115568
PCT Pub. Date: Aug. 6, 2015

(65) Prior Publication Data
US 2016/0369228 A1    Dec. 22, 2016

(30) Foreign Application Priority Data

Jan. 29, 2014  (JP) .................................. 2014-014996
Apr. 16, 2014  (JP) .................................. 2014-085040

(51) Int. Cl.
| C12M 1/38 | (2006.01) |
| C12M 3/00 | (2006.01) |
| C12N 5/00 | (2006.01) |
| C08F 220/24 | (2006.01) |
| C08F 2/54 | (2006.01) |
| C08F 220/22 | (2006.01) |
| C12M 1/26 | (2006.01) |
| C12M 1/00 | (2006.01) |
| C08F 220/54 | (2006.01) |
| G01N 25/20 | (2006.01) |
| G01N 33/44 | (2006.01) |

(52) U.S. Cl.
CPC .............. *C12N 5/0068* (2013.01); *C08F 2/54* (2013.01); *C08F 220/24* (2013.01); *C08F 220/54* (2013.01); *C12M 1/38* (2013.01); *C12M 3/00* (2013.01); *C12M 23/20* (2013.01); *C12M 33/00* (2013.01); *G01N 25/20* (2013.01); *G01N 33/442* (2013.01); *C12N 2509/00* (2013.01); *C12N 2523/00* (2013.01); *C12N 2533/30* (2013.01); *C12N 2537/00* (2013.01)

(58) Field of Classification Search
CPC .. C08F 220/24; C08F 220/56; C12N 2539/10; C12N 5/0068; C12N 2523/00; C12M 23/20
See application file for complete search history.

(56) References Cited

U.S. PATENT DOCUMENTS

| 2003/0099709 A1 | 5/2003 | Shah et al. |
| 2010/0216242 A1 | 8/2010 | Shimizu et al. |
| 2011/0033932 A1 | 2/2011 | Kira et al. |
| 2013/0005039 A1* | 1/2013 | Duschl ................ C12N 5/0068 435/377 |
| 2014/0335610 A1 | 11/2014 | Fukumori et al. |

FOREIGN PATENT DOCUMENTS

| EP | 0 382 214 A1 | 8/1990 |
| EP | 0387975 A1 | 9/1990 |
| EP | 1739143 A1 | 1/2007 |
| GB | 2 248 628 A | 4/1992 |
| JP | 2-211865 A | 8/1990 |
| JP | 4-141084 A | 5/1992 |
| JP | 2002-533377 A | 10/2002 |
| JP | 2005-253305 A | 9/2005 |
| JP | 2006-174826 A | 7/2006 |
| JP | 2007-187647 A | 7/2007 |
| JP | 2008-297488 A | 12/2008 |
| JP | 2009-131275 A | 6/2009 |
| JP | 2011-078316 A | 4/2011 |
| JP | 2013-116130 A | 6/2013 |
| WO | 99/08960 A1 | 2/1999 |
| WO | 2009/119913 A1 | 10/2009 |
| WO | 2013/056312 A1 | 4/2013 |

(Continued)

OTHER PUBLICATIONS

Akane Kitamura et al., "Ion Beam Shosha ni yoru Fusso-kei Kobunshi Zairyo Hyomen no Keijo Jiko Soshikika Seigyo", Dai 13 Kai Hoshasen Process Symposium, Nov. 12, 2009, p. 22, http://www.riken.jp/ap/doc/20091113kitamura.pdf.

Kazuo Sugiyama et al., "Preparation of Poly(methyl methacrylate-co-1H,1H,7H-dodecafluoroheptyl methacrylate) Microspheres as Biomedical Materials", Kinki University Research Institute of Fundamental Technology for Next Generation Hokoku, 2012, pp. 39-46, vol. 3, http://kuring.hiro.kindai.ac.jp/hokoku/data03/039.pdf.

Kansai Bureau Economy, Trade and Industry, Suminoe Textile Co., Ltd., Senryakuteki Kiban Gijutsu Kodoka Shien Jigyo "Ito eno Renzokushiki Denshisen Graft Jugoho ni yoru Ko-Taikyusei Kino Sen'i Kaihatsu", May 2013, Kenku Kaihatsu Seika-To Hokokusho, pp. 1-54, http://www.chusho.meti.go.jp/keiei/sapoin/portal/seika/2010/22152914120.pdf.

(Continued)

*Primary Examiner* — Ramsey Zacharia
(74) *Attorney, Agent, or Firm* — Sughrue Mion, PLLC

(57) ABSTRACT

A temperature-responsive substrate having on its surface a layer containing at least one polymer, the at least one polymer being responsive to temperature and containing a fluorine-containing monomer-derived unit. Also disclosed is a polymer and composition for use in producing the substrate, as well as methods for producing, using and evaluating the substrate.

13 Claims, 9 Drawing Sheets

(56) References Cited

FOREIGN PATENT DOCUMENTS

WO 2013/073707 A1 5/2013

OTHER PUBLICATIONS

Grafton Laboratories Kabushiki Kaisha, "Hoshasen Graft Jugoho o Mochiita Koseino Kagaku Kyuchakuzai GRAFTON", Mar. 30, 2010, pp. 1-4, http://www.nbci.jp/file/100330-2.pdf.

Masaru Tanaka, Biointerface ni Oite Soshikika sareta Mizu Bunshi no Kino, Senryakuteki Sozo Kenkyu Suichin Jigyo Sakigake Kenkyu Hokokusho, Aug. 2005, pp. 24-33, http://jstore.jst.go.jp/PDFView.html?type=research&id=3090&property=researchReportPdfList&index=o.

Thermo Fisher Scientific K.K., "Cell Culture Surface Treatment", Catalog for cell culture-related products, 2013, p. 3.

Z. Yablonka-Reuveni et al., "Skeletal muscle cell populations: Separation and Partial characterization of fibroblast-like cells from embryonic tissue using density centrifugation", Histochemistry, 1987, pp. 27-38, vol. 87, No. 1.

Yuanyuan An et al., "Fluorine-containing thermo-sensitive microgels as carrier systems for biomacromolecules", Colloids and Surfaces B: Biointerfaces, 2012, pp. 246-253, vol. 92.

Hideyuki Hatakeyama et al., "Bio-functionalized thermoresponsive interfaces facilitating cell adhesion and proliferation", Biomaterials, 2006, pp. 5069-5078, vol. 27.

Fei Song et al., "Fabrication of novel thermo-responsive electrospun nanofibrous mats and their application in bioseparation", European Polymer Journal, 2011, pp. 1885-1892, vol. 47.

International Search Report for PCT/JP2015/052579 dated Apr. 21, 2015.

Koji Honda et al., "Effect of [alpha]-substituents on molecular motion and wetting behaviors of poly(fluoroalkyl acrylate) thin films with short fluoroalkyl side chains", Polymer, Elsevier Science Publishers B.V, GB, vol. 55, No. 24, Oct. 7, 2014, pp. 6303-6308, XP029092631.

Communication dated Sep. 5, 2017, from European Patent Office in counterpart application No. 15742799.8.

\* cited by examiner

TEMPERATURE-RESPONSIVE BASE MATERIAL, METHOD FOR PRODUCING SAME, AND METHOD FOR EVALUATING SAME

CROSS REFERENCE TO RELATED APPLICATIONS

This application is a National Stage of International Application No. PCT/JP2015/052579 filed Jan. 29, 2015, claiming priority based on Japanese Patent Application Nos. 2014-014996 filed Jan. 29, 2014 and 2014-085040 filed Apr. 16, 2014, the contents of all of which are incorporated herein by reference in their entirety.

TECHNICAL FIELD

The present invention relates to a temperature-responsive substrate, a production method therefor, and an evaluation method therefor.

BACKGROUND ART

Temperature-responsive substrates have been used for various purposes. For example, such substrates have been used as cell culture substrates, as explained below, as well as column chromatography fillers, systems of drug delivery (drug delivery systems, hydrogels, ion-exchange resins, membrane separation systems, desert-greening materials, water- and oil-repellents, and the like.

Culturing of adherent cells has been performed by attaching the adherent cells onto a glass surface or variously treated synthetic resin surfaces. For example, culture vessels having various surfaces, such as surfaces formed by hydrophilizing polystyrene by glow discharge or corona discharge, and surfaces formed by coating polystyrene with collagen or a biocompatible polymer, such as an MPC polymer, have been used (Patent Literature (PTL) 1, Non-patent Literature (NPL) 1).

To harvest cells cultured by attachment to the surface of such a material (a cell culture substrate), it is necessary to detach the cells from the surface of the cell culture substrate. To achieve this purpose, substances such as trypsin or like proteases or chemicals, having a function of disrupting binding between cells and the cell culture substrate, are used. However, enzyme treatments and chemical treatments are complicated, and are also noted to have disadvantages such as high probability of contamination and likelihood of impairing cells' natural functions due to their degeneration.

In recent years, in the field of regenerative medicine, 3D culture, etc., attention has been given to a sheet-like cell aggregate (a cell sheet), which is formed by attaching cells to each other through an extracellular matrix. However, a cell sheet, once formed on the surface of a cell culture substrate, has been difficult to harvest in the form of an intact cell sheet because enzyme treatments and chemical treatments disrupt the extracellular matrix, as well.

To overcome these drawbacks, there has been proposed a technique of detaching cells through temperature change by using a cell culture substrate coated with a temperature-responsive polymer having an upper critical solution temperature (sometimes abbreviated hereinafter as UCST) or a lower critical solution temperature (sometimes abbreviated hereinafter as LCST) of 0 to 80° C. has been proposed (PTL 2). This temperature-responsive polymer-coated cell culture substrate not only allows harvesting of cells with less damage, but is also effective for producing a cell sheet.

However, there is leeway to further improve conventional temperature-responsive polymer-coated cell culture substrates in terms of cell detachability. More specifically, conventional temperature-responsive polymer-coated cell culture substrates have a problem in that a cell sheet may be broken when detached. This is attributed to the sea-island structure of temperature-responsive polymer coatings (PTL 3). Specifically, the island-shaped crystal portion is weak in cell detachment function because grafting does not easily progress in this portion, whereas the sea-like monomer solution portion is strong in cell detachment function because grafting readily progresses in this portion. When using such a temperature-responsive polymer-coated cell culture substrate, cells cannot be uniformly attached or grown. To solve this problem, optimizing irradiation conditions and drying conditions has been proposed (PTL 3).

CITATION LIST

Patent Literature

PTL 1: JP2008-297488A
PTL 2: JPH2-211865A
PTL 3: JP2013-116130A

Non-Patent Literature (NPL)

Non-patent Literature (NPL) 1: Catalog for cell culture-related products 2013, Thermo Fisher Scientific K.K., Lab products business headquarters, p. 3

SUMMARY OF INVENTION

Technical Problem

An object of the present invention is to provide a temperature-responsive substrate that is superior to conventional temperature-responsive substrates. More specifically, an object of the present invention is to provide a temperature-responsive substrate having the following excellent properties:
(1) an object adhered to the substrate surface (e.g., cells) can be more easily detached; and/or
(2) a sheet adhered to the substrate surface (e.g., a cell sheet) can be detached with less damage; and/or
(3) the substrate has a lower LCST than that of conventional substrates, and is easier to handle.
Another object of the present invention is to provide (4) a method for evaluating a temperature-responsive substrate in terms of the properties described above.

Solution to Problem

The present inventors found that the above object (1) can be achieved by using at least one polymer that is responsive to temperature and that comprises a fluorine-containing monomer-derived unit.

Further, the present inventors thought that forming a more uniform temperature-responsive polymer layer on a substrate would be important to achieve the above object (2). The present inventors found that the object (2) can be achieved by forming a temperature-responsive polymer layer on the substrate surface by radiation surface graft polymerization using a pre-irradiation method.

The present inventors further found that the above object (3) can be achieved by using a temperature-responsive polymer comprising a fluorine-containing monomer-derived unit having a fluorine concentration within a specific range (a fluorine-containing temperature-responsive polymer).

Further, the present inventors found that when a temperature-responsive polymer is used as a temperature-responsive cell culture substrate, the following (a) and (b) are associated with the ease of detachment of an object adhered to the substrate surface (e.g., cells):
(a) difference in water contact angle of the temperature-responsive polymer between specific temperatures; and
(b) presence or absence of a peak of intermediate water in differential scanning calorimetry of the temperature-responsive polymer.

The inventors further found that the above object (4) can be achieved by applying this finding.

Specifically, the present invention provides the following temperature-responsive substrate, production method therefor, and evaluation method therefor.

Item 1. A temperature-responsive substrate having on its surface a layer comprising at least one polymer, said at least one polymer being responsive to temperature and comprising a fluorine-containing monomer-derived unit.

Item 2. The temperature-responsive substrate according to Item 1, wherein the temperature-responsive polymer has a lower critical solution temperature (LCST) of 0 to 15° C.

Item 3. The temperature-responsive substrate according to Item 1 or 2, wherein the temperature-responsive polymer contains fluorine in an amount of 2 to 40 wt. %, based on the weight of the polymer.

Item 4. The temperature-responsive substrate according to any one of Items 1 to 3, wherein the fluorine-containing monomer contains a fluoroalkyl group.

Item 5. The temperature-responsive substrate according to any one of Items 1 to 4, wherein the fluorine-containing monomer is represented by formula (1):

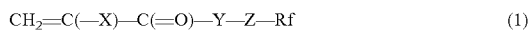

(wherein X is hydrogen, a $C_{1-21}$ linear or branched alkyl group, fluorine, chlorine, bromine, iodine, $CFX^1X^2$— (wherein $X^1$ and $X^2$ are hydrogen, fluorine, chlorine, bromine, or iodine), cyano, a $C_{1-21}$ linear or branched fluoroalkyl group, a substituted or unsubstituted benzyl group, or a substituted or unsubstituted phenyl group;
Y is —O— or —NH—;
Z is a $C_{1-10}$ aliphatic group, a $C_{6-10}$ aromatic group, or a $C_{6-10}$ cyclic aliphatic group, —$CH_2CH_2N(R^1)SO_2$— (wherein $R^1$ is a $C_{1-4}$ alkyl group), —$CH_2CH(OZ)^1)CH_2$— (wherein $Z^1$ is hydrogen or acetyl), —$(CH_2)_m$—$SO_2$—$(CH_2)_n$—, —$(CH_2)_m$—S—$(CH_2)_n$— (wherein m is 1 to 10, and n is 0 to 10), or —$(CH_2)_m$—COO— (wherein m is 1 to 10);
Rf is a $C_{1-20}$ linear or branched fluoroalkyl group optionally containing a heteroatom).

Item 6. The temperature-responsive substrate according to Item 5, wherein Rf in the fluorine-containing monomer represented by formula (1) is a $C_{1-6}$ linear or branched fluoroalkyl group optionally containing a heteroatom.

Item 7. The temperature-responsive substrate according to any one of Items 1 to 6, wherein the layer comprises a blend polymer comprising at least one polymer comprising a fluorine-containing monomer-derived unit in an amount of at least 5 mol %, based on the sum of all monomer units, and at least one temperature-responsive polymer comprising a fluorine-containing monomer-derived unit in an amount of less than 5 mol %, based on the sum of all monomer units.

Item 8. The temperature-responsive substrate according to Item 7, wherein said at least one polymer comprising a fluorine-containing monomer-derived unit in an amount of at least 5 mol %, based on the sum of all monomer units is a temperature-responsive polymer.

Item 9. The temperature-responsive substrate according to Item 7 or 8, wherein the proportion of the fluorine-containing monomer-derived unit is 0.5 to 10 mol %, based on the sum of all monomer units constituting the blend polymer.

Item 10. A polymer comprising a fluorine-containing monomer-derived unit, the polymer being for use in producing the temperature-responsive substrate according to any one of Items 1 to 9.

Item 11. The polymer according to Item 10, which is a temperature-responsive polymer.

Item 12. A composition for use in producing the temperature-responsive substrate according to any one of Items 1 to 9, the composition comprising (a) a monomer, a homopolymer obtained by polymerizing the monomer being responsive to temperature, and (b) a fluorine-containing monomer.

Item 13. A temperature-responsive substrate having on its surface a layer comprising a temperature-responsive polymer, the substrate being obtainable by forming the layer on the substrate surface by radiation surface graft polymerization using a pre-irradiation method.

Item 14. The temperature-responsive substrate according to any one of Items 1 to 9 and 13, which is a cell culture substrate.

Item 15. A method for detaching cells from a culture substrate, comprising detaching the cells, which are cultured on a surface of the temperature-responsive substrate according to any one of Items 1 to 9, from the surface in a temperature environment lower than that of the LCST of the temperature-responsive polymer.

Item 16. The method according to Item 15, wherein the LCST of the temperature-responsive polymer is 0 to 15° C.

Item 17. The method according to Item 16, wherein the temperature-responsive polymer contains fluorine in an amount of 2 to 20 wt. %, based on the weight of the polymer.

Item 18. A method for producing a cell sheet, comprising detaching a sheet of cells, which are cultured on a surface of the temperature-responsive substrate according to any one of Items 1 to 9, from the surface in a temperature environment lower than that of the LCST of the temperature-responsive polymer.

Item 19. The method according to Item 18, wherein the temperature-responsive polymer has an LCST of 0 to 15° C.

Item 20. The method according to Item 19, wherein the temperature-responsive polymer contains 2 to 20 wt. % of fluorine, based on the weight of the polymer.

Item 21. A method for producing a temperature-responsive substrate having a temperature-responsive polymer-containing layer on its surface, comprising forming the layer on the substrate surface by radiation surface graft polymerization using a pre-irradiation method.

Item 22. A temperature-responsive substrate having on its surface a layer comprising a temperature-responsive polymer, wherein when the polymer is prepared by solution polymerization, the difference Δθ between the water contact angle of the polymer at 5° C. (when the polymer has an LCST of less than 20° C.) or at 20° C. (when the polymer has an LCST of at least 20° C., but not more than 37° C.) and the water contact angle of the polymer at 40° C. is 30° or more, and a peak of intermediate water is observed in differential scanning calorimetry of the polymer.

Item 23. A method for evaluating a temperature-responsive substrate having a temperature-responsive polymer-containing layer on its surface, wherein the substrate is evaluated using the polymer prepared by solution polymerization as a sample and evaluation is made based on:

(a) difference Δθ in the water contact angle of the polymer before and after temperature response; and
(b) presence or absence of a peak of intermediate water in differential scanning calorimetry of the sample.

Advantageous Effects of Invention

According to the present invention, properties of a temperature-responsive substrate are improved. More specifically, the following properties are improved: (1) an object adhered to the surface (e.g., cells) can be more easily removed; and/or (2) a sheet adhered to the surface (e.g., a cell sheet) can be detached with less damage; and/or (3) the substrate has a lower LCST than that of conventional materials, and is easier to handle. Furthermore, according to another aspect of the present invention, (4) a temperature-responsive substrate can be evaluated more accurately than ever before.

DESCRIPTION OF EMBODIMENTS

Figure 1:
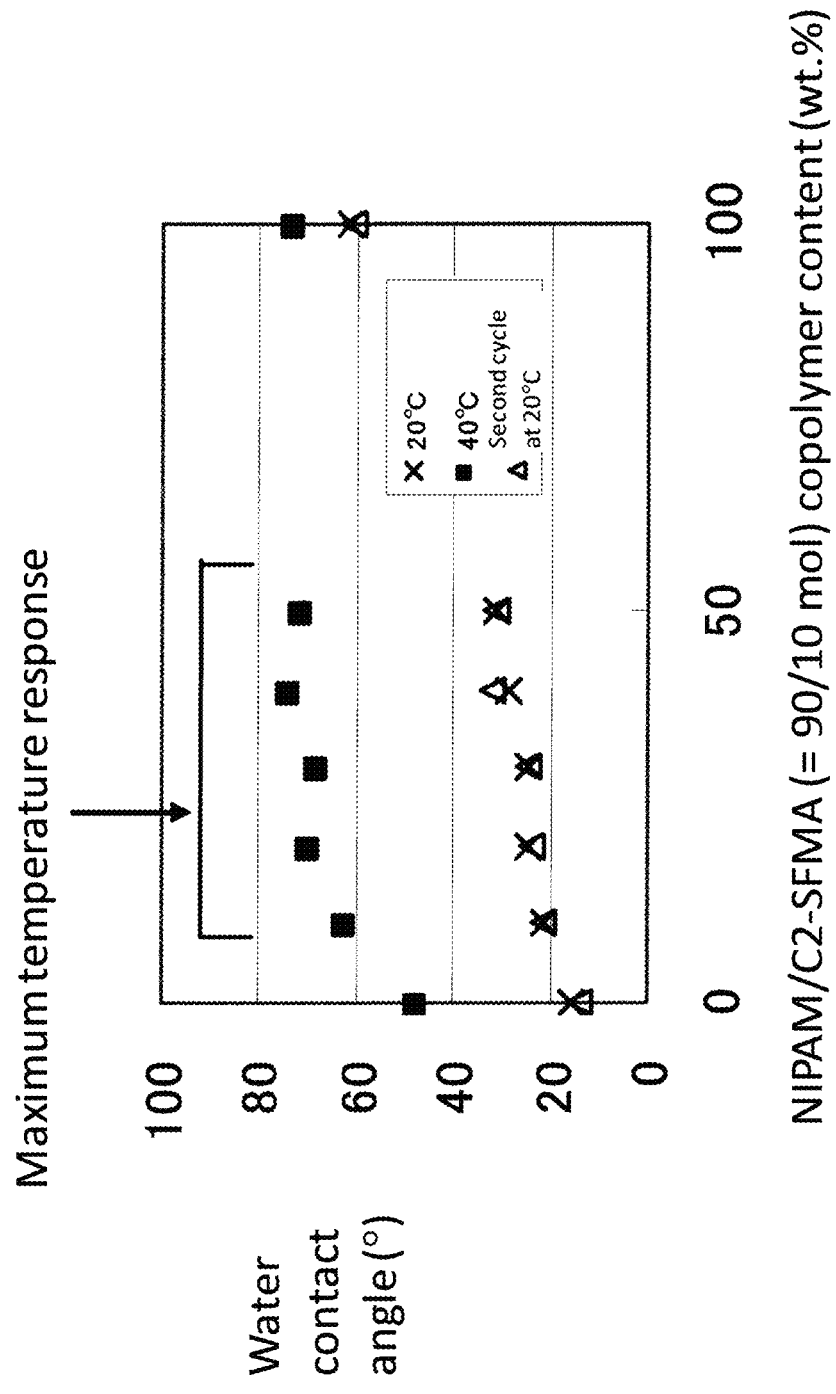
FIG. 1 is a graph showing the evaluation results of temperature response of a blend polymer of "NIPAM homopolymer-NIPAM/C2-SFMA (=90/10 mol) copolymer."
Figure 2:
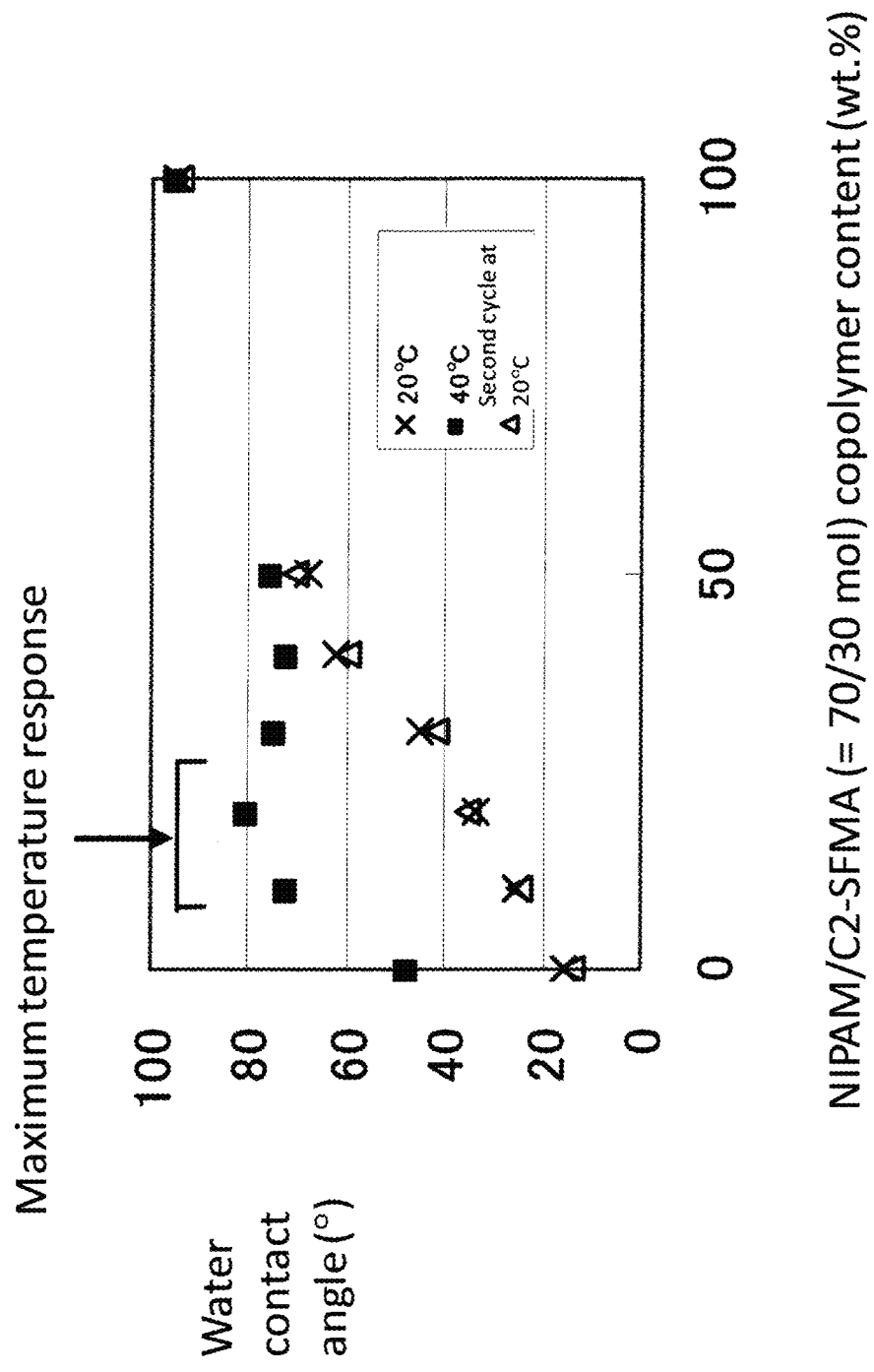
FIG. 2 shows the evaluation results of temperature response of a blend polymer of "NIPAM homopolymer-NIPAM/C2-SFMA (=70/30 mol) copolymer" prepared by solution polymerization.
Figure 3:
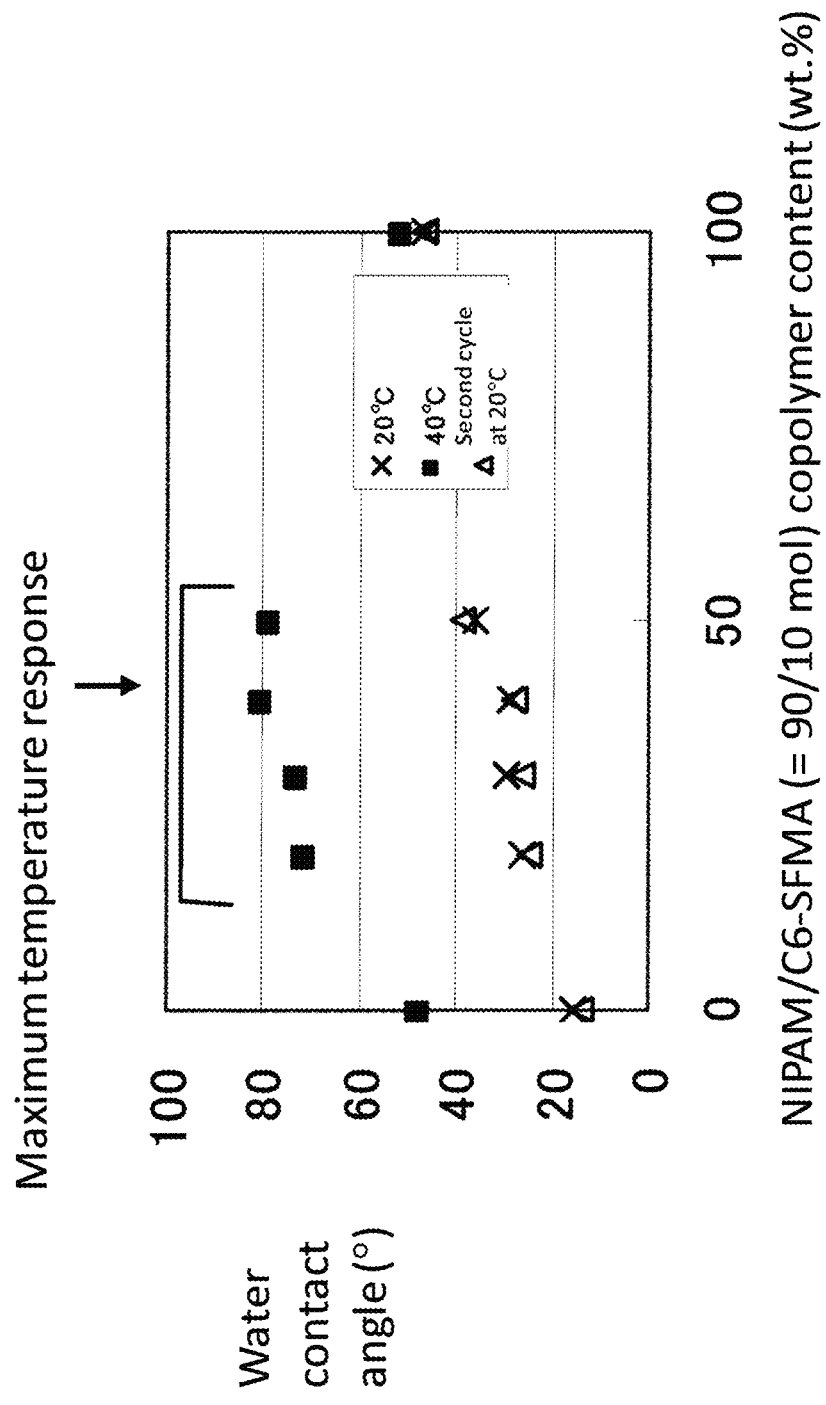
FIG. 3 shows the evaluation results of "NIPAM homopolymer-NIPAM/C6-SFMA (=90/10 mol) copolymer" prepared by solution polymerization.
Figure 4:
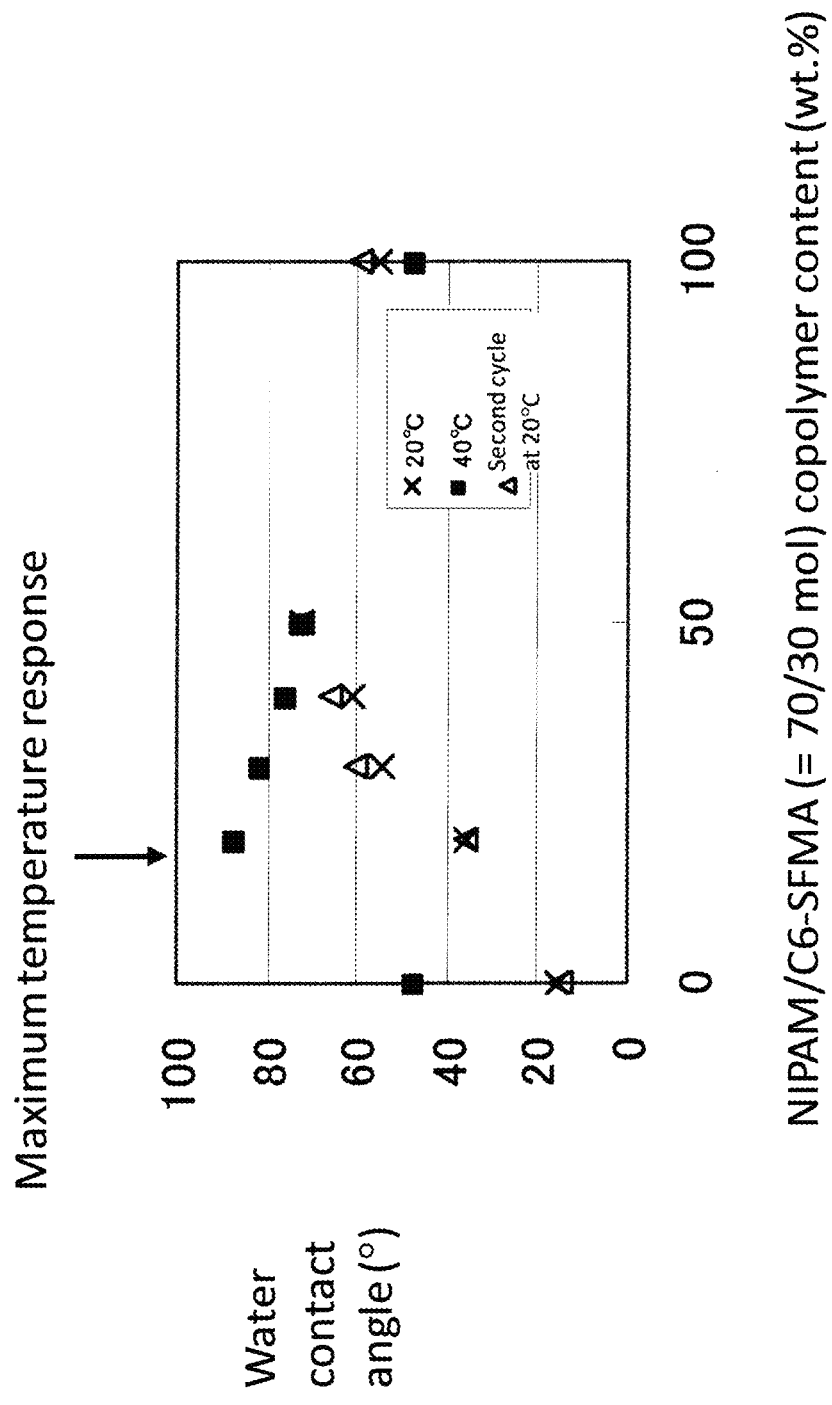
FIG. 4 is a graph showing the evaluation results of temperature response of a blend polymer of "NIPAM homopolymer-NIPAM/C6-SFMA (=70/30 mol) copolymer" prepared by solution polymerization.

The temperature-responsive substrate, the production method therefor, and evaluation method therefor are described more specifically below.

1. Temperature-Responsive Substrate

The temperature-responsive substrate of the present invention has a temperature-responsive polymer-containing layer on its surface.

The temperature-responsive substrate according to one embodiment of the present invention (embodiment 1) is a temperature-responsive substrate having on its surface a layer comprising at least one polymer (sometimes referred to herein as a temperature-responsive polymer layer). The at least one polymer is responsive to temperature, and comprises a fluorine-containing monomer-derived unit.

When the temperature-responsive polymer layer comprises two or more types of polymers, the layer contains a blend of these polymers.

The temperature-responsive substrate according to this embodiment of the present invention comprises a temperature-responsive polymer layer comprising a fluorine-containing monomer-derived unit. Based on this feature, the temperature-responsive substrate of the present invention has an advantageous effect in that objects adhered to its surface (e.g., cells) can be easily detached.

According to another embodiment of the present invention (embodiment 2), the temperature-responsive polymer of the temperature-responsive substrate has an LCST of 0 to 15° C. This is advantageous because detachment of an object adhered to the surface (e.g., cells) can be controlled to take place only in a temperature range lower than that of conventional substrates. For example, when the temperature-responsive substrate of the present invention is used as a cell culture substrate, detachment of cells from the culture substrate does not take place at around room temperature, and can be controlled to take place only at intentionally lower temperatures. In conventional techniques, avoiding unintentional detachment during operation at room temperature has been difficult. According to this embodiment of the present invention, the unintentional detachment can be avoided, and ease of handling can be enhanced.

The temperature-responsive substrate according to another embodiment of the present invention (embodiment 3) is a temperature-responsive substrate that has a temperature-responsive polymer-containing layer on its surface, and can be obtained by forming the layer on the substrate surface by radiation surface graft polymerization using a pre-irradiation method.

Polymerization initiation points are formed on the substrate, and a temperature-responsive polymer can be grown from the polymerization initiation points, by radiation surface graft polymerization using a pre-irradiation method. This enables immobilization of the temperature-responsive polymer on the substrate surface via a chemical bond and formation of a more uniform temperature-responsive polymer layer on the substrate, and is thus preferable. In this specification, "chemical bond" includes covalent bonding, coordinate bonding, ionic bonding, hydrogen bonding, and Van der Waals bonding.

The temperature-responsive substrate according to another embodiment (embodiment 4) of the present invention is a temperature-responsive substrate having a temperature-responsive polymer-containing layer on its surface; when the polymer is prepared by solution polymerization, the difference Δθ between the water contact angle of the polymer at 5° C. (when the polymer has an LCST of less than 20° C.) or at 20° C. (when the polymer has an LCST of at least 20° C., but not more than 37° C.) and the water contact angle of the polymer at 40° C. is 30° or more, and a peak of intermediate water is observed in differential scanning calorimetry of the polymer.

In the above, when Δθ is 300 or more, the temperature-responsive polymer is considered to have a good basic property of firmly attaching an object (e.g., adherent cells) in one temperature region and detaching the attached object (e.g., cells) in another temperature region.

1.1 Temperature-Responsive Polymer

In the present invention, the property of being hydrophobic at a specific temperature and becoming hydrophilic in response to temperature change is referred to as "temperature-responsive," and a polymer having this property may be referred to as a "temperature-responsive polymer." When the temperature-responsive substrate of the present invention is used as a temperature-responsive cell culture substrate, the substrate according to one embodiment may become responsive at a temperature between the cell culture temperature (typically about 37° C., although not limited thereto) and room temperature (typically 20 to 25° C.). In this case, the substrate preferably has an LCST of 28 to 35° C. In another embodiment (embodiment 2), described in detail below, the temperature-responsive substrate may be responsive in a lower temperature region (0 to 15° C.). In this case, the LCST is preferably 6 to 15° C.

The temperature-responsive polymer changes from hydrophobic to hydrophilic (or from hydrophilic to hydrophobic) at the critical solution temperature (CST) in water. The temperature-responsive polymer may be (1) a temperature-responsive polymer that is hydrophilic at a temperature lower than the critical solution temperature (this temperature is particularly referred to as "lower critical solution temperature (LCST)"), and is hydrophobic at a temperature equal to or higher than the LCST; or (2) a temperature-responsive polymer that is hydrophilic at a temperature equal to or higher than the critical solution temperature (this temperature is particularly referred to as "upper critical solution temperature (UCST)"), and is hydrophobic at a temperature lower than the UCST.

The temperature-responsive substrate of the present invention has the following property: since the surface of the substrate to which an object (e.g., adherent cells) adheres (e.g., a surface on which cells are cultured (hereinafter sometimes referred to as "culture surface")) is hydrophobic in a specific temperature region (e.g., cell culture temperature), the object (e.g., adherent cells) can be adhered thereto; whereas, since the surface becomes hydrophobic in response to temperature change, the adhered object (e.g., adherent cells) can be easily detached from the surface (this temperature is referred to as "detachment temperature" for convenience).

When the temperature-responsive substrate of the present invention is used as a cell culture substrate, the detachment temperature is preferably lower than the cell culture temperature from the viewpoint of ease of the cell harvesting procedure after the culture cells are detached from the culture surface, although not limited thereto. In other words, the temperature-responsive polymer for use in this cell culture substrate has an LCST lower than the cell culture temperature. In this case, the LCST is preferably a temperature that does not cause damage to cells. Specifically, 0° C. or more is preferable.

When the temperature-responsive substrate of the present invention is used as a cell culture substrate, the detachment temperature may be higher than the cell culture temperature. In other words, the temperature-responsive polymer for use in this cell culture substrate has a UCST higher than the cell culture temperature. In this case, the UCST is preferably a temperature that does not cause damage to cells. Specifically, the UCST is preferably 80° C. or less, and more preferably 50° C. or less.

Examples of temperature-responsive polymers include, but are not limited to, acrylic polymers, methacrylic polymers, and the like. Specific examples include, but are not limited to, poly(N-isopropylacrylamide (sometimes referred to herein as "NIPAM") (LCST=32° C.), poly(N-n-propylacrylamide) (LCST=21° C.), poly(N-n-propylmethacrylamide) (LCST=32° C.), poly(N-ethoxyethylacrylamide) (LCST=about 35° C.), poly(N-tetrahydrofurfurylacrylamide) (LCST=about 28° C.), poly(N-tetrahydrofurfurylmethacrylamide) (LCST=about 35° C.), poly(N,N-diethylacrylamide) (LCST=32° C.), poly(N-ethylacrylamide), poly(N-isopropylmethacrylamide), poly(N-cyclopropylacrylamide), poly(N-cyclopropylmethacrylamide), poly(N-acryloylpyrrolidine), poly(N-acryloyl piperidine), polymethyl vinyl ether, and the like.

Other examples of temperature-responsive polymers include alkyl-substituted cellulose derivatives such as methylcellulose, ethylcellulose, and hydroxypropylcellulose; polyalkylene oxide block copolymers such as block copolymers of polypropylene oxide and polyethylene oxide; polyalkylene oxide block copolymers; and the like.

These temperature-responsive polymers are not particularly limited and can be obtained, for example, by polymerizing a monomer by radiation or by solution polymerization. The solution polymerization can be performed, for example, in a flask, although not limited thereto.

Examples of usable monomers include monomers whose homopolymers obtained by polymerizing the monomers are responsive to temperature (sometimes referred to as "temperature-responsive monomer" for convenience). Examples of temperature-responsive monomers include, but are not limited to, (meth)acrylamide compounds, N-(or N,N-di) alkyl-substituted (meth)acrylamide derivatives, (meth)acrylamide derivatives having cyclic groups, vinyl ether derivatives, and the like. The temperature-responsive polymer may be a homopolymer obtained by polymerizing one type of temperature-responsive monomer, or a copolymer obtained by polymerizing two or more types of temperature-responsive monomers. The copolymer may be a graft copolymer, a block copolymer, or a random copolymer.

The temperature-responsive polymer may be a copolymer obtained by polymerizing a monomer component comprising, in addition to a temperature-responsive monomer, a monomer that is not a temperature-responsive monomer (sometimes referred to as a "non-temperature-responsive monomer" for convenience) in an amount that does not impair the temperature response. The copolymer may be a random copolymer, a block copolymer, or a graft copolymer. The "random copolymer" as used herein does not strictly mean a copolymer defined by a statistical sequence, but refers, in a broad sense, to any copolymer obtained by subjecting a mixture of two or more types of polymers to simultaneous polymerization, which is not strict polymerization. The following polymer (embodiment 4) is also included in the scope of random copolymers in a broad sense: when a polymer is produced by solution polymerization, the difference $\Delta\theta$ between the water contact angle of the polymer at 5° C. (when the polymer has an LCST of less than 20° C.) or at 20° C. (when the polymer has an LCST of at least 20° C., but not more than 37° C.) and the water contact angle of the polymer at 40° C. is 30° or more, and a peak of intermediate water is observed in differential scanning calorimetry of the polymer. In the monomer group used in the present invention, a random copolymer has an effect of lowering the LCST.

The block polymer may be an AB-type diblock copolymer or an ABA-type triblock copolymer. In the latter case, the polymer comprising a fluorine-containing monomer may be an A block or a B block. Although not limited thereto, the base polymer of a graft polymer may be linear, as disclosed in Macromolecules, 2010, 43, pp. 1964-1974; or may be branched, as disclosed in WO2014/133168. In this case, the fluorine-containing monomer may be copolymerized with a monomer forming a base polymer portion, or may be copolymerized with a temperature-responsive monomer forming a graft polymer portion. The block copolymer and the graft copolymer may be immobilized on a substrate by merely applying the copolymer to the substrate without the radiation step described below. The "immobilization" refers to a state adsorbed in such a manner that the polymer does not elute in a medium during cell culturing, and is not released together with a cell sheet when the cell sheet is detached.

In the above, the proportion of the non-temperature-responsive monomer relative to all monomer components may be appropriately set within a range that does not impair the temperature response of the temperature-responsive monomer. The proportion of the non-temperature-responsive monomer is preferably 30 mol % or less, and more preferably 10 mol % or less, based on all monomer components.

Examples of non-temperature-responsive monomers include, but are not limited to, fluorine-containing monomers. When a fluorine-containing monomer is used as a non-temperature-responsive monomer, the temperature-responsive polymer contains a fluorine-containing monomer-derived unit. In this case, (1) the temperature-responsive polymer, which has properties as a fluorine-containing polymer, in particular, low surface free energy properties, is advantageous in terms of non-adhesiveness when an object (e.g., adherent cells) is brought into contact with the surface (for example, when cells are cultured). In this point, the temperature-responsive polymer is preferably a graft copolymer obtained by subjecting a monomer component comprising at least one temperature-responsive monomer and a fluorine-containing monomer to surface graft polymerization because properties as a fluorine-containing polymer can be more strongly imparted. The temperature-responsive polymer obtained by using a fluorine-containing monomer as a non-temperature-responsive monomer has another advantage in that (2) due to the properties as a fluorine-containing polymer, in particular, insolubility in water, the risk of elution into a medium or release together with a cell sheet upon detaching the cell sheet can be reduced, even without chemical bonding to the substrate surface.

The fluorine-containing monomer is not particularly limited, and may be any monomer that can impart advantageous properties as mentioned above to the final temperature-responsive polymer.

Examples of fluorine-containing monomers include, but are not limited to, acrylic acid monomers, acrylate monomers, acrylamide monomers, styrene monomers, acrylonitrile monomers, vinylpyrrolidone monomers, vinyl ether monomers, pyrrole monomers, and like monomers, wherein at least one hydrogen atom is replaced with a fluorine atom.

Examples of acrylic acid monomers include, but are not limited to, acrylic acid, methacrylic acid, itaconic acid, maleic anhydride, maleic acid, fumaric acid, crotonic acid, and the like.

Examples of acrylate monomers include, but are not limited to, α,β-ethylenically unsaturated carboxylic acid esters, such as methyl acrylate, methyl methacrylate, ethyl acrylate, ethyl methacrylate, n-propylacrylate, n-propylmethacrylate, isopropyl acrylate, isopropyl methacrylate, lauryl acrylate, and stearyl acrylate; hydroxy alkyl esters of α,β-ethylenically unsaturated carboxylic acid esters, such as 2-hydroxylethyl acrylate, 2-hydroxyethyl methacrylate, and 3-hydroxypropyl; and alkoxyalkyl esters of α,β-ethylenically unsaturated carboxylic acid esters, such as diethylene glycol methacrylate.

Examples of acrylamide monomers include, but are not limited to, acrylamide and methylolmethacrylamide.

Examples of styrene monomers include, but are not limited to, styrene and alkyl styrene.

Examples of fluorine-containing monomers include acrylic acid esters having a fluoroalkyl group bonded directly or via a divalent organic group through ester bonding or amide bonding and optionally having a substituent at position a (hereinafter sometimes abbreviated as "fluoroalkyl-containing acrylic acid esters"), or "fluoroalkyl-containing acrylamides," and the like.

Specific examples of preferable fluoroalkyl-containing acrylic acid esters or fluoroalkyl-containing acrylamides include acrylic acid esters represented by formula (1):

$$CH_2=C(-X)-C(=O)-Y-Z-Rf \quad (1)$$

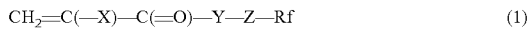

(wherein X is hydrogen, $C_{1-21}$ linear or branched alkyl, fluorine, chlorine, bromine, iodine, $CFX^1X^2-$ (wherein $X^1$ and $X^2$ are hydrogen, fluorine, chlorine, bromine, or iodine), cyano, $C_{1-21}$ linear or branched fluoroalkyl, substituted or unsubstituted benzyl, or substituted or unsubstituted phenyl; Y is —O— or —NH—;

z is a $C_{1-10}$ aliphatic group, a $C_{6-10}$ aromatic or cyclic aliphatic group, $-CH_2CH_2N(R^1)SO_2-$ (wherein $R^1$ is $C_{1-4}$ alkyl), $-CH_2CH(OZ)^1CH_2-$ (wherein $Z^1$ is hydrogen or acetyl), $-(CH_2)_m-SO_2-(CH_2)_n-$, $-(CH_2)_m-S-(CH_2)_n-$ (wherein m is 1 to 10, n is 0 to 10), or $-(CH_2)_m-COO-$ (m is 1 to 10); and Rf is a $C_{1-20}$ linear or branched fluoroalkyl group optionally having a hetero atom), and acrylamides.

The fluoroalkyl group represented by Rf in formula (1) is an optionally heteroatom-containing alkyl group in which one or more hydrogen atoms are replaced by fluorine atoms. Examples of fluoroalkyl groups include optionally heteroatom-containing perfluoroalkyl groups in which all hydrogen atoms are replaced by fluorine atoms.

Acrylic acid esters and acrylamides represented by formula (1) are preferably those in which Rf is a $C_{1-6}$ linear or branched fluoroalkyl group, particularly a $C_{1-3}$ linear or branched perfluoroalkyl group. This is because although the E.P.A. (U.S. Environmental Protection Agency) has recently stated that compounds having a perfluoroalkyl group containing 8 carbon atoms or more are compounds with a high environmental impact that threaten to decompose and accumulate in the environment or the body, this environmental problem has not been cited in regards to acrylic acid esters or acrylamides represented by formula (1), wherein Rf is a $C_{1-6}$ linear or branched fluoroalkyl group.

Examples of the Rf group in formula (1) above include $-CF_3$, $-CF_2CF_3$, $-CF_2CF_2H$, $-CF_2CF_2CF_3$, $-CF_2CFHCF_3$, $-CF(CF_3)_2$, $-CF_2CF_2CF_2CF_3$, $-CF_2CF(CF_3)_2$, $-C(CF_3)_3$, $-(CF_2)_4CF_3$, $-(CF_2)_2CF(CF_3)_2$, $-CF_2C(CF_3)_3$, $-CF(CF_3)CF_2CF_2CF_3$, $-(CF_2)_5CF_3$, $-(CF_2)_3CF(CF_3)_2$, and the like.

The fluorine-containing monomer is preferably a non-telomer. From this viewpoint, the Rf group is preferably a $C_{1-2}$ fluoroalkyl group, or two or more $C_{1-3}$ fluoroalkyl groups attached via a heteroatom. Specific examples include $C_3F_7OCF(CF_3)CF_2OCF(CF_3)-$, $(CF_3)_2NC_nF_{2n}-$ (n=1 to 6), and the like.

Specific examples of acrylic acid esters and acrylamides represented by formula (1) above include the following.

$CH_2=C(-H)-C(=O)-O-(CH_2)_2-Rf$, 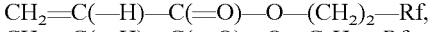
$CH_2=C(-H)-C(=O)-O-C_6H_4-Rf$, 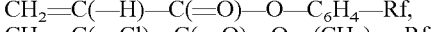
$CH_2=C(-Cl)-C(=O)-O-(CH_2)_2-Rf$, 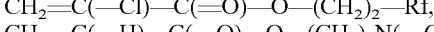
$CH_2=C(-H)-C(=O)-O-(CH_2)_2N(-CH_3)SO_2-Rf$, 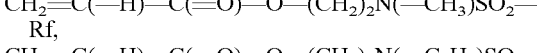
$CH_2=C(-H)-C(=O)-O-(CH_2)_2N(-C_2H_5)SO_2-Rf$, 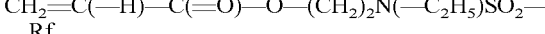
$CH_2=C(-H)-C(=O)-O-CH_2CH(-OH)CH_2-Rf$, 
$CH_2=C(-H)-C(=O)-O-CH_2CH(-OCOCH_3)CH_2-Rf$, 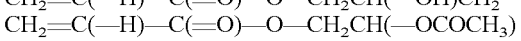
$CH_2=C(-H)-C(=O)-O-(CH_2)_2-S-Rf$ 

$CH_2=C(-H)-C(=O)-O-(CH_2)_2-S-(CH_2)_2-Rf$,
$CH_2=C(-H)-C(=O)-O-(CH_2)_3-SO_2-Rf$,
$CH_2=C(-H)-C(=O)-O-(CH_2)_2-SO_2-(CH_2)_2-Rf$,
$CH_2=C(-H)-C(=O)-NH-(CH_2)_2-Rf$,
$CH_2=C(-CH_3)-C(=O)-O-(CH_2)_2-Rf$,
$CH_2=C(-CH_3)-C(=O)-O-C_6H_4-Rf$,
$CH_2=C(-CH_3)-C(=O)-O-(CH_2)_2N(-CH_3)SO_2-Rf$,
$CH_2=C(-CH_3)-C(=O)-O-(CH_2)_2N(-C_2H_5)SO_2-Rf$,
$CH_2=C(-CH_3)-C(=O)-O-CH_2CH(-OH)CH_2-Rf$,
$CH_2=C(-CH_3)-C(=O)-O-CH_2CH(-OCOCH_3)CH_2-Rf$,
$CH_2=C(-CH_3)-C(=O)-O-(CH_2)_2-S-Rf$,
$CH_2=C(-CH_3)-C(=O)-O-(CH_2)_2-S-(CH_2)_2-Rf$,
$CH_2=C(-CH_3)-C(=O)-O-(CH_2)_3-SO_2-Rf$,
$CH_2=C(-CH_3)-C(=O)-O-(CH_2)_2-SO_2-(CH_2)_2-Rf$,
$CH_2=C(-CH_3)-C(=O)-NH-(CH_2)_2-Rf$,
$CH_2=C(-F)-C(=O)-O-(CH_2)_2-S-Rf$,
$CH_2=C(-F)-C(=O)-O-(CH_2)_2-S-(CH_2)_2-Rf$,
$CH_2=C(-F)-C(=O)-O-(CH_2)_2-SO_2-Rf$,
$CH_2=C(-F)-C(=O)-O-(CH_2)_2-SO_2-(CH_2)_2-Rf$,
$CH_2=C(-F)-C(=O)-NH-(CH_2)_2-Rf$,
$CH_2=C(-Cl)-C(=O)-O-(CH_2)_2-S-Rf$,
$CH_2=C(-Cl)-C(=O)-O-(CH_2)_2-S-(CH_2)_2-Rf$,
$CH_2=C(-Cl)-C(=O)-O-(CH_2)_2-SO_2-Rf$,
$CH_2=C(-Cl)-C(=O)-O-(CH_2)_2-SO_2-(CH_2)_2-Rf$,
$CH_2=C(-Cl)-C(=O)-NH-(CH_2)_2-Rf$,
$CH_2=C(-CF_3)-C(=O)-O-(CH_2)_2-S-Rf$,
$CH_2=C(-CF_3)-C(=O)-O-(CH_2)_2-S-(CH_2)_2-Rf$,
$CH_2=C(-CF_3)-C(=O)-O-(CH_2)_2-SO_2-Rf$,
$CH_2=C(-CF_3)-C(=O)-O-(CH_2)_2-SO_2-(CH_2)_2-Rf$,
$CH_2=C(-CF_3)-C(=O)-NH-(CH_2)_2-Rf$,
$CH_2=C(-CF_2H)-C(=O)-O-(CH_2)_2-S-Rf$,
$CH_2=C(-CF_2H)-C(=O)-O-(CH_2)_2-S-(CH_2)_2-Rf$,
$CH_2=C(-CF_2H)-C(=O)-O-(CH_2)_2-SO_2-Rf$,
$CH_2=C(-CF_2H)-C(=O)-O-(CH_2)_2-SO_2-(CH_2)_2-Rf$,
$CH_2=C(-CF_2H)-C(=O)-NH-(CH_2)_2-Rf$,
$CH_2=C(-CN)-C(=O)-O-(CH_2)_2-S-Rf$,
$CH_2=C(-CN)-C(=O)-O-(CH_2)_2-S-(CH_2)_2-Rf$,
$CH_2=C(-CN)-C(=O)-O-(CH_2)_2-SO_2-Rf$,
$CH_2=C(-CN)-C(=O)-O-(CH_2)_2-SO_2-(CH_2)_2-Rf$,
$CH_2=C(-CN)-C(=O)-NH-(CH_2)_2-Rf$,
$CH_2=C(-CF_2CF_3)-C(=O)-O-(CH_2)_2-S-Rf$,
$CH_2=C(-CF_2CF_3)-C(=O)-O-(CH_2)_2-S-(CH_2)_2-Rf$,
$CH_2=C(-CF_2CF_3)-C(=O)-O-(CH_2)_2-SO_2-Rf$,
$CH_2=C(-CF_2CF_3)-C(=O)-O-(CH_2)_2-SO_2-(CH_2)_2-Rf$,
$CH_2=C(-CF_2CF_3)-C(=O)-NH-(CH_2)_2-Rf$,
$CH_2=C(-F)-C(=O)-O-(CH_2)_3-S-Rf$,
$CH_2=C(-F)-C(=O)-O-(CH_2)_3-S-(CH_2)_2-Rf$,
$CH_2=C(-F)-C(=O)-O-(CH_2)_3-SO_2-Rf$,
$CH_2=C(-F)-C(=O)-O-(CH_2)_3-SO_2-(CH_2)_2-Rf$,
$CH_2=C(-F)-C(=O)-NH-(CH_2)_3-Rf$,
$CH_2=C(-Cl)-C(=O)-O-(CH_2)_3-S-Rf$,
$CH_2=C(-Cl)-C(=O)-O-(CH_2)_3-S-(CH_2)_2-Rf$,
$CH_2=C(-Cl)-C(=O)-O-(CH_2)_3-SO_2-Rf$,
$CH_2=C(-Cl)-C(=O)-O-(CH_2)_3-SO_2-(CH_2)_2-Rf$,
$CH_2=C(-CF_3)-C(=O)-O-(CH_2)_3-S-Rf$,
$CH_2=C(-CF_3)-C(=O)-O-(CH_2)_3-S-(CH_2)_2-Rf$,
$CH_2=C(-CF_3)-C(=O)-O-(CH_2)_3-SO_2-Rf$,
$CH_2=C(-CF_3)-C(=O)-O-(CH_2)_3-SO_2-(CH_2)_2-Rf$,
$CH_2=C(-CF_2H)-C(=O)-O-(CH_2)_3-S-Rf$,
$CH_2=C(-CF_2H)-C(=O)-O-(CH_2)_3-S-(CH_2)_2-Rf$,
$CH_2=C(-CF_2H)-C(=O)-O-(CH_2)_3-SO_2-Rf$,
$CH_2=C(-CF_2H)-C(=O)-O-(CH_2)_3-SO_2-(CH_2)_2-Rf$,
$CH_2=C(-CN)-C(=O)-O-(CH_2)_3-S-Rf$,
$CH_2=C(-CN)-C(=O)-O-(CH_2)_3-S-(CH_2)_2-Rf$,
$CH_2=C(-CN)-C(=O)-O-(CH_2)_3-SO_2-Rf$,
$CH_2=C(-CN)-C(=O)-O-(CH_2)_3-SO_2-(CH_2)_2-Rf$
$CH_2=C(-CF_2CF_3)-C(=O)-O-(CH_2)_3-S-Rf$,
$CH_2=C(-CF_2CF_3)-C(=O)-O-(CH_2)_3-S-(CH_2)_2-Rf$,
$CH_2=C(-CF_2CF_3)-C(=O)-O-(CH_2)_3-SO_2-Rf$, and
$CH_2=C(-CF_2CF_3)-C(=O)-O-(CH_2)_2-SO_2-(CH_2)_2-Rf$ (wherein Rf is a $C_{1-6}$, preferably $C_{1-3}$, fluoroalkyl group); and $C_3F_7OCF(CF_3)CF_2O-CF(CF_3)CH_2$-MAc,
$C_3F_7OCF(CF_3)CF_2O-CF(CF_3)CH_2$-Ac,
$(CF_3)_2CH$-Ac,
$C_2F_5CH_2$-MAc, and
$C_2F_5CH_2$-Ac (wherein Ac is acrylate and MAc is methacrylate).

The fluoroalkyl-containing acrylic acid esters and fluoroalkyl-containing acrylamides can be used singly, or in a combination of two or more.

The surface layer of the temperature-responsive substrate of the present invention particularly preferably comprises a blend polymer containing (i) at least one polymer containing a fluorine-containing monomer-derived unit in a proportion of at least 5 mol %, based on the sum of all monomer units, and (ii) at least one temperature-responsive polymer containing a fluorine-containing monomer-derived unit in a proportion of less than 5%, based on the sum of all monomer units, because the temperature-responsive substrate exhibits particularly excellent detachability. In this case, the proportion of the fluorine-containing monomer-derived unit based on the sum of all monomer units constituting the polymer (i) is preferably 5 to 45 mol %. Other examples of preferable ranges include, but are not limited to, 10 to 45 mol %, 10 to 40 mol %, 10 to 30 mol %, and the like. The proportion can be appropriately set. The proportion of the fluorine-containing monomer-derived unit, based on the sum of all monomer units constituting the temperature-responsive polymer (ii) is not particularly limited. The lower the proportion of the fluorine-containing monomer-derived unit, the more preferable. The proportion may be 0 mol %. Although there is no particular limitation, the proportion may be, for example, in the range of 0 to 3 mol %, 0 to 2 mol %, or 0 to 1 mol %.

In view of detachability, the proportion of the fluorine-containing monomer-derived unit, based on the sum of all monomer units constituting the blend polymer is 0.5 to 10 mol %, and particularly 0.5 to 5 mol %. Alternatively, the glass transition temperature (Tg) of the polymer (i) can also be used as an index. Specifically, it is preferable in terms of detachability that the polymer (i) have a glass transition temperature (Tg) of 20 to 130° C., and more preferably 50 to 120° C. The glass transition temperature herein means an extrapolated glass transition end temperature ($T_{eg}$) as defined in the "Testing Methods for Transition Temperatures of Plastics" of JIS K7121-1987.

1.2 Temperature-Responsive Polymer Layer

The temperature-responsive polymer-containing layer (temperature-responsive polymer layer) contains a temperature-responsive polymer as an essential component, and may further contain a polymer that is not responsive to temperature (sometimes referred to as a "non-temperature-responsive polymer").

Such a non-temperature-responsive polymer is not particularly limited, and can be selected from a broad range. Although not limited thereto, the non-temperature-responsive polymer may be a polymer containing a non-temperature-responsive monomer-derived unit described above for temperature-responsive polymers. The non-temperature-responsive polymer may be a homopolymer or a copolymer. When the non-temperature-responsive polymer is a copolymer, the polymer may be a graft copolymer, block copolymer, or a random copolymer.

The non-temperature-responsive polymer may be any polymer that is not responsive to temperature. As long as the polymer is not responsive to temperature, the polymer may contain the temperature-responsive monomer-derived units described above for temperature-responsive polymers.

The non-temperature-responsive polymer may contain a fluorine-containing monomer-derived unit. The fluorine-containing monomer is not particularly limited and may be, for example, a fluorine-containing monomer described above for temperature-responsive polymers. The non-temperature-responsive polymer may consist of a fluorine-containing monomer-derived unit.

When the temperature-responsive polymer layer consists of a temperature-responsive polymer alone, the temperature-responsive polymer of the temperature-responsive polymer layer is typically adsorbed on the substrate surface in an amount of 1 to 10 µg/cm$^2$, although not limited thereto. An adsorption of 1 µg/cm$^2$ or more facilitates the detachment of an object (e.g. cells) from the temperature-responsive polymer when the polymer becomes hydrophilic in response to temperature. An adsorption of 10 µg/cm$^2$ or less facilitates the detachment of an object (e.g. cells) when the polymer is hydrophobic before responding to temperature.

When the temperature-responsive substrate of the present invention is used as a cell culture substrate, the temperature-responsive polymer may be adsorbed on the substrate surface in an amount of 10 µg/cm$^2$ or more, if the surface of the temperature-responsive polymer layer is further coated with a cell adhesion protein. In this case, the amount of the temperature-responsive polymer is preferably 50 µg/cm$^2$ or less. When the surface is coated with a cell adhesion protein, the amount of the temperature-responsive polymer is preferably 50 µg/cm$^2$ or less because it facilitates the adhesion of cells. The coating may be performed in accordance with a conventional method. A typical method comprises coating the substrate surface with an aqueous solution of a cell adhesion protein, then removing the aqueous solution, and rinsing the coated surface.

The cell adhesive protein can be of any type without particular limitation, and may be, for example, collagen, laminin, laminin 5, fibronectin, or the like. These proteins may be used singly, or in a combination of two or more. Preparations containing an extracellular matrix protein (e.g., Matrigel® etc.) can also be used.

When the temperature-responsive polymer layer further contains a non-temperature-responsive polymer, the temperature-responsive polymer content may be appropriately adjusted by varying the proportion of the temperature-responsive polymer in the entire polymer blend, with reference to the content described above for the temperature-responsive polymer layer consisting only of a temperature-responsive polymer.

The amount of the temperature-responsive polymer in the temperature-responsive polymer layer is measured using FT-IR-ATR. The coating amount of the cell adhesion protein is also measured using FT-IR-ATR.

1.3 Method for Producing Temperature-Responsive Polymer

Although the method for producing the temperature-responsive polymer is not particularly limited, the temperature-responsive polymer can be obtained by polymerizing a monomer component comprising at least one temperature-responsive monomer and optionally further comprising at least one non-temperature-responsive monomer.

More specifically, the temperature-responsive polymer can be obtained by a method comprising the steps of:
(1) dissolving the above monomer component in a solvent; and
(2) polymerizing the monomer component in the solvent obtained in step (1) above.

The solvent used for dissolving the monomer component in step (1) is not particularly limited. For example, solvents having a boiling point of 120° C. or less, in particular, 60 to 110° C., at normal temperature are preferable. Specific examples include methanol, ethanol, n-(or i-)propanol, 2-(or n-)butanol, water, and the like. The solvent for dissolving the above monomer component may be one solvent, or a mixture of two or more solvents. When two or more solvents are mixed, at least one solvent selected from 1-pentanol, 2-ethyl-1-butanol, 2-butoxyethanol, and ethylene (or diethylene)glycol, monoethyl ether, and the like may further be mixed. The solvent may further contain one or more additives, if necessary. Examples of such additives include, but are not limited to, acids such as sulfuric acid, Mohr's salts, and the like.

(i) A temperature-responsive polymer or (ii) a copolymer comprising a temperature-responsive monomer and a fluorine-containing monomer may be dissolved in an amount of, for example, 0.1 to 90 wt. %, preferably 0.1 to 50 wt. %, and more preferably 0.1 to 10 wt. %, relative to the monomer.

In the polymerization step (2), the substrate surface may first be coated with a monomer component dissolved in a solvent, and then the polymerization may be performed to form a temperature-responsive polymer on the surface; or the polymerization may be first performed to form a temperature-responsive polymer, and then the substrate surface may be coated with the obtained temperature-responsive polymer.

The polymerization method is not particularly limited, and examples of usable methods include radical polymerization using electron beam (EB) irradiation, γ-ray irradiation, ultraviolet irradiation, plasma treatment, corona treatment, organic polymerization reaction, etc.

The method for coating the substrate surface with a preformed temperature-responsive polymer is not particularly limited, and the coating may be performed, for example, by mere physical adsorption through application, kneading or the like, or may be performed by further subjecting the coated substrate to electron beam (EB) irradiation, γ-ray irradiation, ultraviolet irradiation, plasma treatment, corona treatment, or the like to immobilize the temperature-responsive polymer on the substrate surface via a chemical bond.

As a method comprising coating the substrate surface with a monomer component dissolved in a solvent and then polymerizing the monomer component to form a temperature-responsive polymer on the surface, surface graft polymerization can be used to form a temperature-responsive polymer layer on the substrate. For this polymerization, any of pre-irradiation and simultaneous irradiation methods can be used.

Radiation surface graft polymerization using a pre-irradiation method is particularly preferable for use to form a temperature-responsive polymer layer on the substrate surface. According to this method, after polymerization initiation points are formed on the substrate surface, a temperature-responsive polymer can be grown from the polymerization initiation point(s). This method is preferable because the temperature-responsive polymer can be immobilized on the substrate surface via a chemical bond.

As described above, when the surface layer of the temperature-responsive substrate of the present invention comprises a blend polymer of (i) at least one polymer containing a fluorine-containing monomer-derived unit in an amount of 5 mol % or more, based on the sum of all monomer units, and (ii) at least one temperature-responsive polymer containing a fluorine-containing monomer-derived unit in an amount of less than 5 mol %, based on the sum of all monomer units, the temperature-responsive substrate provides particularly excellent detachability, and is thus preferable. Such a temperature-responsive substrate can be obtained, for example, by allowing a polymerization reaction to proceed in the presence of a fluorine-free temperature-responsive monomer (and, if necessary, a small amount of a fluorine-containing monomer) and a temperature-responsive polymer (i) on the surface, although not limited thereto. A fluorine-free temperature-responsive monomer (and, if necessary, a small amount of a fluorine-containing monomer) is thereby polymerized to obtain a temperature-responsive polymer (ii) on the substrate, thus forming a blend polymer of the polymer (i) and the temperature-responsive polymer (ii) on the surface. Further, this blend polymer is preferably bound to the surface via a chemical bond.

When the surface layer of the temperature-responsive substrate of the present invention comprises a blend polymer of polymers (i) and (ii) as described above, a blend polymer obtained in the following manner is particularly preferable in view of better temperature response: the polymers (i) and (ii) are individually obtained by a method such as solution polymerization in a flask and then applied in a blended state to the surface or kneaded, optionally followed by a further treatment to immobilize this blend polymer on the surface.

In the above process, the application or kneading method is not particularly limited. Examples of usable methods include spin coating, dipping, spraying, brushing, and the like. The application or kneading can be performed after dissolving each polymer in a suitable solvent, if necessary.

The solvent used in the above step is not particularly limited, and can be suitably selected according to the physical properties of the polymer. For example, isopropyl alcohol, ethanol, and like solvents mentioned as examples in "1.3 Method for producing the temperature-responsive polymer" can be used. The amount of polymers dissolved in the solvent is not particularly limited, and the total amount of the polymers may be, for example, 0.1 to 20 wt. %, and preferably 1 to 10 wt. %.

The treatment for immobilizing the blend polymer on the surface is not particularly limited. Examples of usable treatments include heating, electron beam irradiation (EB), γ-ray irradiation, ultraviolet irradiation, plasma treatment, corona treatment, and the like. Each polymer can be immobilized on the surface via a chemical bond by using these treatments.

1.4 Embodiment 2

Embodiment 2 is the above temperature-responsive substrate that comprises a temperature-responsive polymer having an LCST of 0 to 15° C. The temperature-responsive substrate having this feature is advantageous in that detachment of an object (e.g., cells) adhered to its surface can be controlled to take place only in a lower temperature region than conventional substrates.

Examples of temperature-responsive polymers having an LCST of 0 to 15° C. include, but are not limited to, polymers having a fluorine content of 2 to 20 wt. %, more preferably 2 to 10 wt. %, based on the polymer weight.

The fluorine-containing temperature-responsive polymer having an LCST of 0 to 15° C. may be a polymer having the structure described above in "1.1 Temperature-responsive polymer."

Examples of the temperature-responsive polymer having an LCST of 0 to 15° C. include, but are not limited to, copolymers of a fluorine-free temperature-responsive monomer and a fluorine-containing non-temperature-responsive monomer. The proportion of fluorine, based on the polymer weight, can be appropriately adjusted by varying the proportion of fluorine in the fluorine-containing non-temperature-responsive monomer and/or the proportion of the fluorine-containing non-temperature-responsive monomer, based on the sum of all monomers.

For example, when a temperature-responsive polymer is produced by using NIPAM as a fluorine-free temperature-responsive monomer and copolymerizing therewith (perfluoroethyl)methyl methacrylate as a fluorine-containing non-temperature-responsive monomer, a temperature-responsive polymer with a critical solution temperature of 0 to 15° C. can be obtained by using the (perfluoroethyl)methyl methacrylate in an amount of 2 to 20 mol %, based on the sum of all monomers.

The copolymer of a fluorine-free temperature-responsive monomer and a fluorine-containing non-temperature-responsive monomer is preferably a copolymer comprising fluoroacrylate as at least a part of a fluorine-containing non-temperature-responsive monomer. Although not limited thereto, the fluoroacrylate may be a compound having the structure explained above in "1.1 Temperature-responsive polymer."

1.5 Substrate

The temperature-responsive substrate of the present invention comprises a temperature-responsive polymer-containing layer on the substrate surface, as described above.

The substrate used in the present invention may be any substrate commonly used, such as base plates, powders, fibers, and membranes.

The substrate preferably contains at least on its surface a material capable of forming a polymerization initiation point by irradiation because a temperature-responsive polymer layer can be formed on the substrate surface by surface graft polymerization, as described above. In this case, the substrate may have only on its surface a material capable of forming a polymerization initiation point, or the entire substrate may have such a material.

Examples of the material capable of forming a polymerization initiation point include, but are not limited to, glass, plastics, ceramics, metals, and the like. Specific examples include acrylic resins such as polystyrene, polyethylene terephthalate, low-density polyethylene, medium-density polyethylene, high-density polyethylene, polyurethane, urethane acrylate, and polymethylmethacrylate; polyamide (nylon), polycarbonate, natural rubber with a conjugated bond, synthetic rubber with a conjugated bond, silicone rubber, and the like. The material may be a blend polymer comprising two or more of these materials, or a polymer alloy.

As long as the effect of the present invention is not impaired, the substrate may be surface-treated or may further comprise other layers, if necessary.

The shape of the substrate is not particularly limited and the substrate can typically be, for example, in the form of dishes, well plates, tubes, bottles, flasks, films used as cell culture and/or medical fluid bags, and the like.

2. Method for Evaluating the Temperature-Responsive Substrate

The method for evaluating the temperature-responsive substrate according to the present invention is a method using as a sample a polymer prepared by solution polymerization as described above and comprising conducting evaluation, based on:

(a) difference $\Delta\theta$ in the water contact angle of the polymer before and after temperature response; and (b) presence or absence of a peak of intermediate water in differential scanning calorimetry of the sample.

The property of firmly attaching an object (e.g., adherent cells) in one temperature region and detaching the attached object (e.g., cells) in another temperature region is a basic property required of temperature-responsive substrates. When a substrate is used as a cell culture substrate, the substrate must be hydrophobic during cell culture and must be hydrophilic during detachment. This evaluation method can evaluate this basic property required of temperature-responsive substrates.

The present inventors found that in the temperature-responsive substrate obtainable by radiation surface graft polymerization, the adsorbed amount of grafted temperature-responsive polymer is very small, and a very thin film is formed; therefore, the temperature response of the contact angle of the adsorbed temperature-responsive polymer layer surface is greatly influenced by the substrate, and cannot be clearly observed. The present inventors found that this evaluation method enables the screening of detachability of an object (e.g., adherent cells) from a temperature-responsive cell culture substrate having this problem. It should be noted that this evaluation is for screening purposes only, and that not all the substrates that pass the screening exhibit good detachability.

2.1 Sample Temperature-Responsive Polymers Prepared by Solution Polymerization In the method for evaluating the temperature-responsive substrate of the present invention, a polymer prepared by solution polymerization as described above is used as a sample.

The solution polymerization method is not particularly limited, but is preferably performed in the same solvent as described in "1.2 Method for producing temperature-responsive polymer."

The method for polymerizing a monomer component in a solvent may be, for example, a method comprising dissolving a monomer component in a solvent, followed by deoxidation, and then adding a radical polymerization initiator while stirring the obtained solution, thus allowing a polymerization reaction to proceed.

The polymerization initiator may be any known polymerization initiator for radical polymerization reactions. Examples of usable polymerization initiators include azo initiators such as azoisobutyrodinitrile, methyl azoisobutyrate, and azobisdimethylvaleronitrile; benzoyl peroxide, potassium persulfate, ammonium persulfate, benzophenone derivatives, phosphine oxide derivatives, benzoketone derivatives, phenylthioether derivatives, azido derivatives, diazo derivatives, disulfide derivatives, and the like. These polymerization initiators can be used singly, or in a combination of two or more.

The amount of the polymerization initiator to be used is not particularly limited. It is usually preferable that the polymerization initiator be used in an amount of about 0.01 to 10 parts by weight, and more preferably about 0.1 to 1 parts by weight, per 100 parts by weight of the monomer component.

Although not limited thereto, the concentration of the monomer component in the solvent is typically preferably about 10 to 50 wt. %, and more preferably about 20 to 40 wt. %.

The polymerization conditions, such as polymerization temperature and polymerization time, may be appropriately adjusted according to the type and amount of monomer component used, the type and amount of polymerization initiator used, etc. The polymerization reaction may typically be performed at a temperature of about 50 to 100° C. at a monomer conversion of about 60 to 100%. The monomer conversion can be calculated from the monomer peak areas before and after the polymerization as determined by gas chromatography.

2.2 Difference in Water Contact Angle $\Delta\theta$

The difference $\Delta\theta$ in water contact angle of the thus-obtained sample before and after temperature response is determined.

Although the measurement method is not particularly limited, the water contact angle is preferably calculated by spin-coating the sample prepared in the above manner to form a film, and measuring the water contact angle of the film.

Although the spin-coating conditions are not particularly limited, the obtained polymer is diluted with a solvent to a specific concentration and spin-coated on a specific substrate; and, if necessary, heat treatment is further performed.

In the above processing, the polymer concentration during the spin-coating is not particularly limited. For example, the concentration may be 1 wt. %.

The solvent is not particularly limited. For example, the solvent may be isopropyl alcohol or the like.

The substrate is not particularly limited. For example, the substrate may be silicon wafer or the like. Although not limited thereto, the silicon wafer may be, for example, a silicon wafer with a native oxide film (surface roughness Ra (arithmetic average roughness): 0.5 nm or less).

The spin-coating conditions are not particularly limited. For example, conditions such as 2000 rpm may be used.

The heat-treatment conditions are not particularly limited. For example, the conditions may be heating at 110° C. for 3 minutes. When the heat treatment is not performed, the coated substrate is maintained in a vacuum desiccator for at least 1 hour while continuously creating a reduced pressure with a vacuum pump in order to distill off the solvent remaining in the spin-coated film.

When $\Delta\theta$ is 30° or more, the temperature-responsive polymer is considered to have a good basic property mentioned above. When $\Delta\theta$ is 40° or more, the temperature-responsive polymer is considered to have a better basic property. When $\Delta\theta$ is 50° or more, the temperature-responsive polymer is considered to have an even better basic property.

When the temperature-responsive substrate of the present invention is used as a cell culture substrate, the temperature-responsive polymer is (1) hydrophobic at temperatures around 37° C., which are normal cell culture temperatures, and becomes (2) hydrophilic in response to temperature change, preferably in response to temperature change within the range of 20° C. Accordingly, to evaluate such temperature-responsive polymers, the following temperature ranges are set for samples obtained in a manner described above: (1) cell culture temperature range: 30 to 50° C., and (2) temperature change range: within ±20° C. from the cell culture temperature range (1), i.e., 10 to 30° C. (a lower temperature range) or 50 to 70° C. (a higher temperature range). The difference $\Delta\theta$ between the water contact angle in the temperature range (1) (30 to 50° C.) and the water contact angle in the temperature range (2) (10 to 30° C. (a lower temperature range) or 50 to 70° C. (a higher temperature range)) is determined. In the above, when the LCST of the temperature-responsive polymer is lower than the culture temperature, the polymer becomes hydrophilic in the lower temperature range. Accordingly, the water contact angle in a lower temperature range is measured as a water contact angle in the temperature range (2). When the UCST of the temperature-responsive polymer is higher than the culture temperature, the polymer becomes hydrophilic in the higher temperature region. Accordingly, the water contact angle in a higher temperature range is measured as a water contact angle in the temperature range (2).

When the LCST of the temperature-responsive polymer is lower than 20° C., the difference $\Delta\theta$ between the water contact angle at 5° C. and the water contact angle at 40° C. is preferably measured. When the LCST of the temperature-responsive polymer is at least 20° C. and not higher than 37° C., the difference $\Delta\theta$ between the water contact angle at 20° C. and the water contact angle at 40° C. is preferably measured.

The method for measuring the water contact angle is not particularly limited. For example, the following method can be used.

After 2 μL of water is added dropwise to the surface of a film formed by spin-coating a sample, the static contact angle is measured using a DropMaster 701 (produced by Kyowa Interface Science Co., Ltd.) fully automatic contact angle meter, or an equivalent thereof. Specifically, the static contact angles at 5° C. and 20° C. are measured after 60 seconds, whereas the static contact angle at 40° C. is measured after 5 seconds.

2.3 Peak of Intermediate Water

The presence or absence of a peak of intermediate water in differential scanning calorimetry of a sample obtained as in the above section 2.1 is investigated.

Intermediate water refers to a water molecule that interacts weakly with a synthetic polymer surface. The presence of this molecule is considered to contribute to preventing the adhesion of, for example, cells and proteins.

Using differential scanning calorimetry (DSC), intermediate water is observed as an exothermic peak (−50 to 0° C.) derived from low-temperature crystal formation when a hydrated polymer is heated from −75° C.

The present inventors found that the presence of intermediate water in a temperature-responsive polymer provides good detachability of an object (e.g., adherent cells) adhered to the surface of a temperature-responsive cell culture substrate comprising the temperature-responsive polymer.

The measurement of intermediate water was performed using a sample obtained as in section 2.1 above. The measurement method is not particularly limited. For example, the following method can be used.

After 0.1 g of a sample obtained as in the above section 2.1 is immersed in 50 g of water at room temperature (20 to 25° C.) for 24 hours and an excess of water is removed with filter paper, 5 mg of a polymer is placed in an aluminum pan. Measurement is performed using a DSC822e (produced by Mettler Toledo), or an equivalent thereof. The low-temperature crystal formation peak detected in the range of 50 to 0° C. during heating of the polymer from −75° C. to 50° C. indicates intermediate water. The conditions for cooling to heating are not particularly limited. For example, the following conditions can be used.

25° C.→−75° C. (cooling with liquid nitrogen)
−75° C. (maintained for 30 minutes)
75° C.→50° C. (temperature increase: 2.5° C./min)

3. Use of Temperature-Responsive Substrate

The temperature-responsive substrate of the present invention can be widely used for the purpose of adhesion of an object to its surface and detachment therefrom. The kind of substrate is not particularly limited and may be, for example, base plates, powders, fibers, membranes, and the like. The use of the substrate is not particularly limited, and the substrate may be used, for example, as cell culture substrates, fillers of column chromatography, drug delivery systems, hydrogels, ion-exchange resins, membrane separation systems, desert-greening materials, water-repellent oil-repellent agents, and the like.

Using the temperature-responsive cell culture substrate of the present invention, a cell sheet can be produced from various cells, such as epithelial cells and endothelial cells forming tissues in a living body or organs; contractile skeletal muscle cells; smooth muscle cells; cardiomyocytes; neurons forming nervous systems; neuroglias; fibroblasts; hepatocytes, which are associated with the metabolism of living bodies; non-hepatocytes and adipocytes; cells having differentiation potentials, such as stem cells that are present in various tissues, marrow cells, and ES cells. The cell sheet thus produced is suitable for use in regenerative medicine, etc. because of intact adhesion factors on the surface, as well as uniform quality of the portion in contact with a cell culture surface. Utilizing such a cell sheet also allows application to detection devices, such as biosensors.

4. Method for Detaching Cells from the Culture Substrate

The present invention includes a method for detaching cells from a culture substrate, the method comprising a step in which cells cultured on the surface of the temperature-responsive substrate of the present invention are detached from the surface in a temperature environment lower than that of the LCST of the temperature-responsive polymer.

The cells may be any anchorage-dependent cells, and are not particularly limited. The source of the cells is also not particularly limited. Cells that are used for various purposes, such as cells for uses ranging from medicine (e.g., regenerative medicine) to experiments, can be used. Any of stem cells, primary culture cells, and established cell lines can be used.

Examples of cells include, but are not limited to, fibroblasts, epidermal cells, epithelial cells (e.g., corneal epithelial cells, bladder epithelial cells, etc.), myoblasts, smooth muscle cells, hepatocytes, endothelial cells, nerve cells, oral mucosa cells, amniocytes, adipocytes (e.g., preadipocytes), dendritic cells (e.g., monocyte-derived cells), osteoclasts, tumor cells, various stem cells (e.g., mesenchymal stem cells, ES cells, and iPS cells), and the like.

The cell culturing conditions can be appropriately set in accordance with a known method depending on the type of cells used.

When a temperature above the LCST of the temperature-responsive polymer changes to a temperature below the LCST, the surface of the temperature-responsive substrate of the present invention changes from hydrophobic during cell culture to hydrophilic during detachment. This facilitates the detachment of cells from the surface. Although it depends on the type of cells and culture conditions, a mere temperature change may cause natural detachment of cells. The detachment can also be appropriately promoted by mechanical stimulation, such as shaking and substrate's expansion and contraction, and/or chemical functions such as trypsin.

The length of time for which cells are allowed to stand in a temperature environment lower than that of the LCST of the temperature-responsive polymer is not particularly limited, and can be appropriately set.

5. Method for Producing Cell Sheet

The present invention includes a method for producing a cell sheet, comprising forming a sheet of cells by culturing cells on the surface of a temperature-responsive substrate of the present invention, and detaching the cell sheet from the surface in a temperature environment lower than that of the LCST of the temperature-responsive polymer.

Examples of usable cells include those described above in "4. Method for detaching cells from the culture substrate." Such cells may be appropriately selected according to culture conditions, as long as the cells can be formed into a sheet.

Specific examples of cells particularly preferable for use in preparing a cell sheet include, but are not limited to, fibroblasts, epidermal cells, epithelial cells (e.g., corneal epithelial cells, bladder epithelial cells, etc.), myoblasts, smooth muscle cells, oral mucosa cells, amnionic cells, adipocytes (e.g., preadipocytes), dendritic cells (e.g., monocyte-derived dendritic cells), osteoclasts, tumor cells, various stem cells (e.g., mesenchymal stem cells, ES cells, and iPS cells), and the like.

The cell sheet may be a single-layer sheet or a laminated sheet.

EXAMPLES

The present invention is described more specifically with reference to Examples. However, the scope of the invention is not limited to these Examples.

1. Examples 1 to 32 and Comparative Examples 1 to 4

1.1 Material

As cell culture substrates (cell culture dishes), Falcon® 3001 Petri dishes (diameter: 3.5 cm) produced by U.S. Corning Incorporated (formerly Becton Dickinson Labware) were used.

1.2 Pre-Irradiation Method

Each dish was irradiated with a dose of 100 kGy of electron beam. Subsequently, 0.12 mL of a 40 wt. % or 60 wt. % diluted solution obtained by diluting each monomer shown in Table 1 with isopropyl alcohol (hereinafter abbreviated as IPA) (in Comparative Examples 3 and 4, however, HCFC225 was used in place of IPA) was injected into the dish, and allowed to stand at room temperature overnight for surface graft polymerization.

1.3 Simultaneous Irradiation Method

A 40 wt. % or 60 wt. % diluted solution obtained by diluting each monomer shown in Table 1 with IPA (in Comparative Examples 3 and 4, however, HCFC225 was used in place of IPA) was injected into the dish in an amount of 0.12 mL. Subsequently, the dish was irradiated with a dose of 100 kGy of electron beam, and then allowed to stand at room temperature overnight for surface graft polymerization.

1.4 Washing after Surface Graft Polymerization

After the surface graft polymerization, each dish was washed with a commercially available wash, and dried at room temperature.

1.5 Preparation of Polymers by Solution Polymerization

Polymerization was performed under the following conditions. When an NIPAM monomer was used, IPA was used as a polymerization solvent. When a fluorinated monomer alone was used, HCFC225 was used as a polymerization solvent. The monomer concentration was set to 20 wt. %. Using azobisisobutyronitrile as a polymerization initiator in an amount of 1 mol % (relative to the monomer used), an NIPMA monomer was polymerized at 70° C. and a fluorinated monomer was polymerized at 50° C.

1.6 Surface Analysis by X-Ray Photoelectron Spectroscopy (XPS)

N1s/C1s and $F_1s/C1s$ were measured at an angle of emission of 900 using ESCA3400 (produced by Shimadzu Corporation). The measurement confirmed that each polymer was grafted on the substrate surface.

1.7 Measurement of Temperature-Dependent Contact Angle of Dish

2 µL of water was added dropwise to the substrate surface, and the static contact angle after 1 second was measured at 5° C., 20° C., and 40° C. using a DropMaster701 (produced by Kyowa Interface Science Co., Ltd.) fully automatic contact angle meter. The measurement at 5° C. was performed in a refrigerator adjusted to a temperature of 5° C. The measurement at 20° C. was performed at room temperature (20° C.). The measurement at 40° C. was performed in the following manner. After a test piece was placed on a hot plate heated to 40° C. and covered with a case of a size to cover the entire test piece, the test piece was allowed to stand for at least 30 minutes. The test piece was then placed on a temperature-controlled stage (40° C.), and measurement was performed.

1.8 Measurement of Temperature-Dependent Contact Angle of the Polymers Prepared by Solution Polymerization The polymer prepared by solution polymerization was diluted to a concentration of 1 wt. % with IPA (in Comparative Examples 3 and 4, however, HCFC225 was used in place of IPA), and spin-coated on a silicon wafer with a natural oxide film (surface roughness Ra (arithmetic average roughness): 0.5 nm or less) at 2,000 rpm and then dried with a vacuum desiccator for 2 hours. The resulting product was used as a sample. The temperature-dependent contact angle was measured in the same manner as the above dish measurement except that the static contact angle measurement at 5° C. and 20° C. was performed 60 seconds after water was added dropwise to the substrate surface, whereas the measurement at 40° C. was performed 5 seconds after water was added dropwise to the substrate surface.

1.9 Measurement of the Glass Transition Point of Polymer Prepared by Solution Polymerization 10 mg of a polymer powder subjected to measurement in a temperature range of −50 to 150° C. at a heating rate of 10° C./min using a DSC822e (produced by Mettler Toledo, Inc., U.S.), and the extrapolated glass transition-ending temperature (JIS K7121-1987) was read from the thermogram of the second cycle.

1.10 Measurement of Molecular Weight of Polymer Prepared by Solution Polymerization The molecular weight of each polymer was measured by gel permeation chromatography (GPC) at a polymer concentration of 0.2 wt. % using N,N-dimethylformamide containing 10 mM LiBr as an eluent. Polyethylene glycol standards were used for calibration.

1.11 Measurement of Intermediate Water

After 0.1 g of a polymer prepared by solution polymerization was immersed in 50 g of water at room temperature (20 to 25° C.) for 24 hours and excess water was removed with filter paper, 5 mg of each polymer was placed into an aluminum pan, and measurement was performed using DSC822e under the following conditions:
room temperature→−75° C. (cooling with liquid nitrogen)
−75° C. (maintained for 30 minutes)
−75° C.→50° C. (temperature rise: 2.5° C./min).
When the temperature was raised from −75° C. to 50° C., a low-temperature crystallization peak detected in the range of −50 to 0° C. indicates intermediate water.

Table 1 shows the evaluation results of polymers prepared by surface graft polymerization of various monomer solutions.

The abbreviations in Table 1 are defined below:
Cn-SF(M)A: (perfluoroalkyl)methyl methacrylate or (perfluoroalkyl)ethyl (meth)acrylate (wherein n represents the number of carbon atoms of the perfluoroalkyl group)
C2-SFMA: (perfluoroethyl)methyl methacrylate
C4-SFMA: (perfluorobutyl)methyl methacrylate
C6-SFMA: (perfluorohexyl)ethyl methacrylate
C2-SFA: (perfluoroethyl)methyl acrylate
C6-SFA: (perfluorohexyl)ethyl acrylate.
Ac of (CF3)2CH—Ac, C3F7OCF(CF3)CF2O—CF(CF3)CH2-Ac, and C3F7OCF(CF3)CF2O—CF(CF3)CH2-MAc represents CH═C(H)COO—, and MAc represents CH═C(CH3)COO—.

As shown in Table 1, the monomers used in Examples 9 to 18 are the same as those used in Examples 1 to 8, respectively. Examples 1 to 8 show experimental results of surface graft polymerization using simultaneous irradiation, whereas Examples 9 to 16 show experimental results of surface graft polymerization using a pre-irradiation method. The results of solution polymerization are shown only in the columns for Examples 1 to 8.

The N1s/C1s and $F_1s/C_1s$ ratios obtained by XPS measurement of the surface prepared by pre-irradiation were higher than those ratios obtained by the measurement of the surface prepared using the same amount of the same monomer by simultaneous irradiation. The results thus suggest that a larger amount of polymer was adsorbed on the surface obtained by pre-irradiation.

TABLE 1

| | Monomer | | | Electron beam irradiation conditions | |
| --- | --- | --- | --- | --- | --- |
| Example | Type | Composition ratio (mol/mol) | Monomer concentration (mass %) | Irradiation method | Irradiation dose (kGy) |
| Example 1 | NIPAM/C2-SFA | 90/10 | 40 | Simultaneous irradiation | 100 |
| Example 2 | NIPAM/C2-SFMA | | | | |
| Example 3 | NIPAM/(CF3)2CH—Ac | | | | |
| Example 4 | NIPAM/C3F7OCF(CF3)CF2O—CF(CF3)CH2—Ac | | | | |
| Example 5 | NIPAM/C3F7OCF(CF3)CF2O—CF(CF3)CH2-Mac | | | | |
| Example 6 | NIPAM/C4-SFA | | | | |
| Example 7 | NIPAM/C6-SFA | | | | |
| Example 8 | NIPAM/C6-SFMA | | | | |
| Example 9 | NIPAM/C2-SFA | | | Pre-irradiation | |
| Example 10 | NIPAM/C2-SFMA | | | | |
| Example 11 | NIPAM/(CF3)2CH—Ac | | | | |
| Example 12 | NIPAM/C3F7OCF(CF3)CF2O—CF(CF3)CH2—Ac | | | | |
| Example 13 | NIPAM/C3F7OCF(CF3)CF2O—CF(CF3)CH2-MAc | | | | |
| Example 14 | NIPAM/C4-SFA | | | | |

TABLE 1-continued

| Example | | 100/0 | | |
|---|---|---|---|---|
| Example 15 | NIPAM/C6-SFA | | | |
| Example 16 | NIPAM/C6-SFMA | | | |
| Example 17 | NIPAM homomonomer | 100/0 | 40 | Pre-irradiation |
| Example 18 | | | 60 | |
| Comparative Example 1 | | | 40 | Simultaneous irradiation |
| Comparative Example 2 | | | 60 | |
| Comparative Example 3 | C4-SFMA homomonomer | | 40 | Pre-irradiation |
| Comparative Example 4 | C6-SFA homomonomer | | | |

| | Film graft-polymerized on the PS surface | | | | | Spin-coated film of the solution polymerization polymer | | | | | | |
|---|---|---|---|---|---|---|---|---|---|---|---|---|
| | XPS | | Contact angle (°) | | | Contact angle (°) | | | | | LSCT | Presence of intermediate |
| Example | N1s/C1s | F1s/C1s | 5° C. | 20° C. | 40° C. | 5° C. | 20° C. | 40° C. | $\theta_{5\to40°C.}$ | $\theta_{20\to40°C.}$ | (° C.) | water |
| Example 1 | 0.06 | 0.11 | 59 | 70 | 72 | 13 | 41 | 65 | 52 | — | 8 | Yes |
| Example 2 | 0.07 | 0.12 | 60 | 72 | 75 | 32 | 82 | 96 | 64 | — | 9 | Yes |
| Example 3 | 0.08 | 0.10 | 61 | 68 | 69 | 21 | 54 | 56 | 35 | — | 8 | Yes |
| Example 4 | 0.07 | 0.21 | 61 | 74 | 76 | 23 | 59 | 61 | 38 | — | 9 | Yes |
| Example 5 | 0.06 | 0.19 | 60 | 73 | 75 | 25 | 60 | 62 | 37 | — | 8 | Yes |
| Example 6 | 0.05 | 0.18 | 63 | 75 | 78 | 31 | 64 | 75 | 44 | — | 10 | Yes |
| Example 7 | 0.06 | 0.28 | 62 | 80 | 82 | 46 | 89 | 94 | 48 | — | 7 | Yes |
| Example 8 | 0.04 | 0.25 | 65 | 77 | 77 | 49 | 96 | 105 | 56 | — | 8 | Yes |
| Example 9 | 0.11 | 0.15 | 58 | 71 | 75 | | | | | | | |
| Example 10 | 0.12 | 0.17 | 57 | 73 | 77 | | | | | | | |
| Example 11 | 0.10 | 0.15 | 60 | 67 | 70 | | | | | | | |
| Example 12 | 0.09 | 0.27 | 59 | 73 | 78 | | | | | | | |
| Example 13 | 0.10 | 0.26 | 60 | 75 | 80 | | | | | | | |
| Example 14 | 0.11 | 0.23 | 58 | 73 | 79 | | | | | | | |
| Example 15 | 0.12 | 0.37 | 62 | 79 | 84 | | | | | | | |
| Example 16 | 0.12 | 0.34 | 60 | 80 | 82 | | | | | | | |
| Example 17 | 0.13 | 0.00 | 59 | 59 | 72 | 6 | 7 | 47 | — | 40 | 32 | Yes |
| Example 18 | 0.15 | 0.00 | 57 | 57 | 74 | | | | | | | Yes |
| Comparative Example 1 | 0.10 | 0.00 | 61 | 60 | 70 | | | | | | | Yes |
| Comparative Example 2 | 0.12 | 0.00 | 62 | 59 | 73 | | | | | | | Yes |
| Comparative Example 3 | 0.00 | 1.10 | 103 | 102 | 105 | 122 | 121 | 123 | — | — | None | No |
| Comparative Example 4 | 0.00 | 1.50 | 104 | 105 | 109 | 115 | 115 | 117 | — | — | None | No |

(Common Experimental Conditions)
Solvent used to dilute monomer: isopropyl alcohol
Amount of monomer solution applied to a 3.5 cm dish (Falcon 3001): 0.12 mL Table 2 shows the relationship between the weight ratio and the molar ratio of NIPAM/Cn-SF(M)A copolymer and NIPAM/n-butyl methacrylate (BMA) copolymer prepared by solution polymerization, fluorine content, and various physical properties.

TABLE 2

| Copolymer | NIPAM/Cn-SF(M)A ratio | | Fluorine content (wt. %) | Glass transition point (° C.) | Molecular weight (on a weight basis) | LCST (° C.) | Remarks |
|---|---|---|---|---|---|---|---|
| | Molar ratio | Weight ratio | | | | | |
| PNIPAM | 100/0 | 100/0 | 0 | 138 | 31.0k | 32 | Example 17, Comparative Example 7 |
| NIPAM/C2-SFA copolymer | 95/5 | 91/9 | 3.8 | 103 | 28.6k | 13 | Example 33 |
| | 90/10 | 83/17 | 7.7 | 79 | 21.2k | 8 | Examples 1 and 34 |
| | 70/30 | 56/44 | 20.1 | 45 | 23.5k | — | |
| NIPAM/C2-SFMA copolymer | 90/10 | 82/18 | 7.2 | 118 | 22.4k | 9 | Example 2 |
| | 70/30 | 55/45 | 19.9 | 92 | 16.1k | — | Example 19 |

TABLE 2-continued

| Copolymer | NIPAM/Cn-SF(M)A ratio Molar ratio | NIPAM/Cn-SF(M)A ratio Weight ratio | Fluorine content (wt. %) | Glass transition point (° C.) | Molecular weight (on a weight basis) | LCST (° C.) | Remarks |
|---|---|---|---|---|---|---|---|
| NIPAM/C6-SFA copolymer | 98/2 | 93/7 | 4.2 | 122 | 28.4k | 12 | Example 35 |
|  | 96/4 | 87/13 | 7.9 | 103 | 22.3k | 8 | Example 36 |
|  | 90/10 | 71/29 | 17.1 | 63 | 18.2k | 7 | Example 7 |
|  | 70/30 | 39/61 | 36.3 | 27 | 14.6k | — |  |
| NIPAM/C6-SFMA copolymer | 90/10 | 70/30 | 16.9 | 101 | 23.8k | 8 | Example 8 |
|  | 70/30 | 38/62 | 35.7 | 73 | 13.2k | — | Example 20 |
| NIPAM/BMA copolymer | 95/5 | 94/6 | 0 | 104 | 33.6k | 21 | Comparative Example 6 |
|  | 90/10 | 88/12 | 0 | 71 | 29.4k | 17 | Comparative Example 7 |

Table 3 to 6 and FIGS. 1 to 4 show the effects of blending of an NIPAM/Cn-SFMA copolymer (wherein n=2 or 6) shown in Table 2 with NIPAM on temperature response. The surface graft polymerization conditions in Tables 3 to 6 are simultaneous irradiation at a monomer concentration of 40 wt. % (see Examples 1.3), and washing after the surface graft polymerization was performed in the same manner as in Example 1.4.

The solution polymerization conditions were the same as in the above section 1.5. The temperature-dependent contact angle was measured in the same manner as in the above section 1.8.

TABLE 3

| Example | NIPAM/C2-SFMA (=90/10 mol) copolymer content (wt. %) | Contact angle (°) (Solution polymerization) 20° C. | 40° C. | $\Delta\theta_{20\to40°\,C.}$ | Blend polymer of NIPMA homopolymer and NIPAM/C2-SFMA (=90/10 mol) copolymer 20° C. | $\Delta\theta_{40\to20°\,C.}$ |
|---|---|---|---|---|---|---|
|  | 0 | 15 | 48 | 32 | 14 | −33 |
| Example 21 | 10 | 21 | 63 | 41 | 22 | −41 |
| Example 22 | 20 | 25 | 70 | 45 | 24 | −46 |
| Example 23 | 30 | 24 | 68 | 44 | 25 | −43 |
| Example 24 | 40 | 29 | 74 | 45 | 32 | −42 |
| Example 25 | 50 | 31 | 71 | 40 | 31 | −40 |
| Example 2 | 100 | 62 | 73 | 12 | 61 | −13 |

As shown in Table 3, the temperature response of NIPAM was enhanced by blending a specific amount of an NIPAM/C2-SFMA (=90/10 mol) copolymer with NIPAM.

TABLE 4

| Example | NIPAM/C2-SFMA (=70/30 mol) copolymer content (wt. %) | Contact angle (°) (Solution polymerization) 20° C. | 40° C. | $\Delta\theta_{20\to40°\,C.}$ | Blend polymer of NIPMA homopolymer and NIPAM/C2-SFMA (=70/30 mol) copolymer 20° C. | $\Delta\theta_{40\to20°\,C.}$ |
|---|---|---|---|---|---|---|
|  | 0 | 15 | 48 | 32 | 14 | −33 |
| Example 26 | 10 | 25 | 73 | 47 | 25 | −48 |
| Example 27 | 20 | 34 | 80 | 46 | 36 | −45 |

As shown in Table 4, the temperature response of NIPAM was enhanced by blending a specific amount of an NIPAM/C2-SFMA (=70/30 mol) copolymer with NIPAM.

TABLE 5

| Example | NIPAM/C6-SFMA (=90/10 mol) copolymer content (wt. %) | Contact angle (°) (Solution polymerization) Blend polymer of NIPMA homopolymer and NIPAM/C6-SFMA (=90/10 mol) copolymer | | | | |
|---|---|---|---|---|---|---|
| | | 20° C. | 40° C. | $\Delta\theta_{20\to40°\,C.}$ | 20° C. | $\Delta\theta_{40\to20°\,C.}$ |
| | 0 | 15 | 48 | 32 | 14 | −33 |
| Example 28 | 20 | 27 | 71 | 45 | 24 | −47 |
| Example 29 | 30 | 29 | 73 | 44 | 26 | −46 |
| Example 30 | 40 | 29 | 80 | 51 | 28 | −52 |
| Example 31 | 50 | 36 | 79 | 42 | 38 | −40 |
| Example 8 | 100 | 46 | 51 | 5 | 47 | −4 |

As shown in Table 5, the temperature response of NIPAM was enhanced by blending a specific amount of an NIPAM/C6-SFMA (=90/10 mol) copolymer with NIPAM.

TABLE 6

| Example | NIPAM/C6-SFMA (=70/30 mol) copolymer content (wt. %) | Contact angle (°) (Solution polymerization) Blend polymer of NIPMA homopolymer and NIPAM/C6-SFMA (=70/30 mol) copolymer | | | | |
|---|---|---|---|---|---|---|
| | | 20° C. | 40° C. | $\Delta\theta_{20\to40°\,C.}$ | 20° C. | $\Delta\theta_{40\to20°\,C.}$ |
| | 0 | 15 | 48 | 32 | 14 | −33 |
| Example 32 | 20 | 35 | 87 | 52 | 36 | −51 |

As shown in Table 6, the temperature response of NIPAM was enhanced by blending a specific amount of an NIPAM/C6-SFMA (=70/30 mol) copolymer with NIPAM.

FIGS. 1 to 4 only show temperature-response enhancement effects under specific conditions (for example, change from one specific temperature to another). FIGS. 1 to 4 show that temperature response was maximized by blending a specific amount of an NIPAM/fluorine-containing monomer copolymer with NIPAM under the specific conditions. Under the other conditions, the amount of the NIPAM/C2-SFMA (=90/10 mol) copolymer to be blended to maximize the temperature response was different. However, there was observed a general trend for temperature response to be enhanced by blending a copolymer of NIPAM and a fluorine-containing monomer. Accordingly, the blend amount can be appropriately set to obtain the enhancement effects under the desired conditions.

2. Test Example 1 (Preparation of Fibroblast Sheet)

Primary fibroblast cells were prepared in accordance with known procedures (Z. Yablonka-Reuveni, M. Nameroff. Skeletal muscle cell populations. Separation and partial characterization of fibroblast-like cells from embryonic tissue using density centrifugation. Histochemistry. 1987; 87: 27-38). Briefly, this is a procedure in which a cell suspension derived from the leg muscle of an 8-week-old Lewis rat is separated into fibroblasts and muscle cells by Percoll® (produced by Amersham Biosciences, Sweden) density centrifugation.

The isolated fibroblasts were cultured on the temperature-responsive cell culture substrate of the present invention. For culturing, a culture medium containing 6% FBS, 40% Medium199 (Gibco® BRL), 0.2% penicillin-streptomycin solution, 2.7 mmol/L glucose, and 54% balanced salt solution (116 mmol/L NaCl, 1.0 mmol/L $NaH_2PO_4$, 0.8 mmol/L $MgSO_4$, 1.18 mmol/L KCl, 0.87 mmol/L $CaCl_2$, and 26.2 mmol/K $NaHCO_3$) was used. After two days of culturing, the temperature was changed to detach the cells as a cell sheet.

3. Example 33

(1) Preparation of Cell Culture Substrate

An IPA solution containing $1\times10^{-4}$ wt. % of an NIPAM/C2-SFA (=95/5 mol) copolymer was prepared. A specific amount of this solution was applied to the culture substrate of a commercially available substrate (Falcon 3001 Petri dish, diameter: 3.5 cm) to form a film of the polymer in an amount of 2.0 μg/cm² in terms of NIPAM component by solvent casting.

After forming the film, the film was irradiated with an electron beam (200 kGy) to immobilize the polymer on the surface of the substrate.

Subsequently, cell culture was performed on the culture surface in the following manner.
Cells used: mouse fibroblasts
Medium used: DMEM/10% FCS
Cell seeding density: $1\times10^5$ cells/dish (diameter: 3.5 cm)

(2) Cell Detachment Test During the Initial Culture Period

Figure 5:
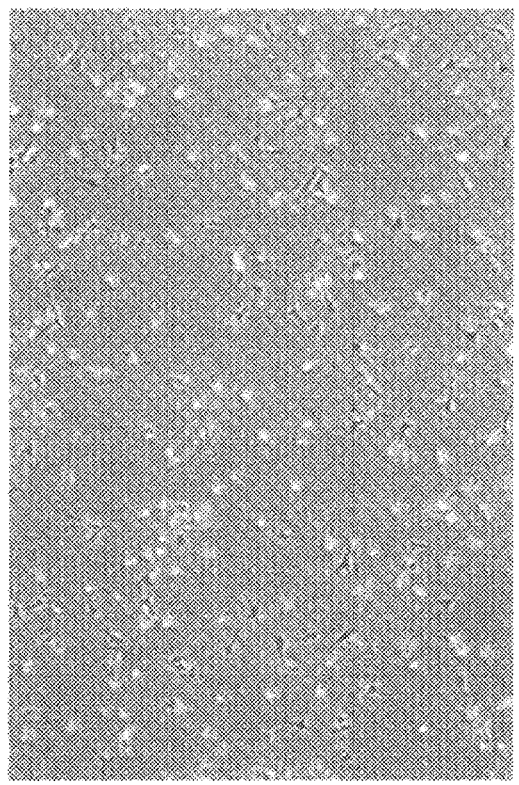
FIG. 5 is a photograph showing the culture experiment in Example 33.

After culture was performed for one day, adhesion of the cell was observed under microscope (FIG. 5). Attachment of the cells to the culture surface was confirmed.

Figure 6:
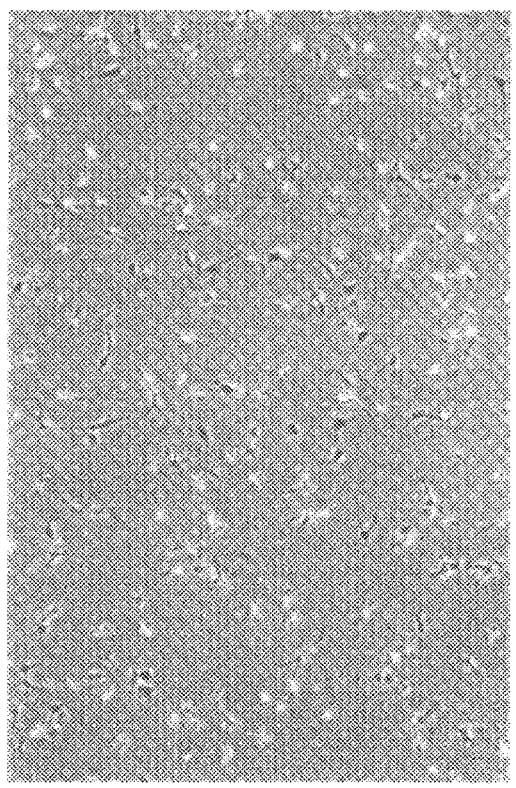
FIG. 6 is a photograph showing the culture experiment in Example 33.

The culture substrate on which cells were cultured was then allowed to stand at 20° C. After 15 minutes, the condition of the cells was observed (FIG. 6). The attachment of the cells to the culture surface was confirmed to be maintained.

Figure 7:
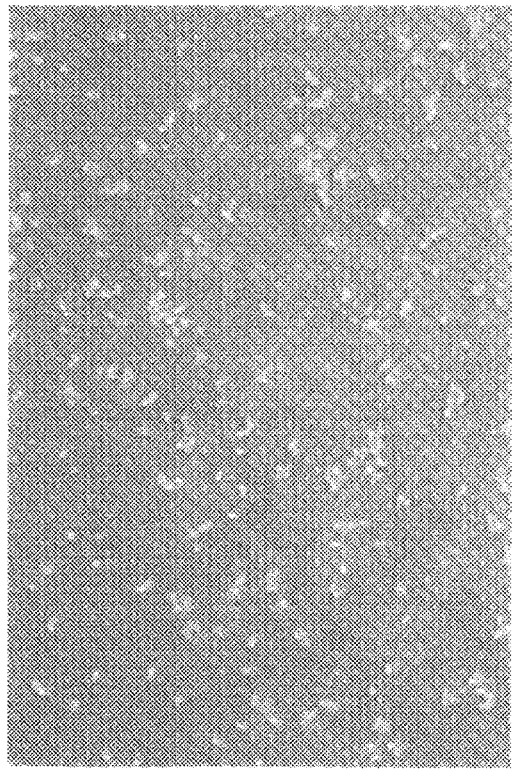
FIG. 7 is a photograph showing the culture experiment in Example 33.

The culture substrate on which cells were cultured was further allowed to stand at 5° C. After 15 minutes, the condition of the cells was observed (FIG. 7). Detachment of the cells from the culture surface was confirmed.

(3) Cell Culture Detachment Test after Long-Term Culture

Figure 8:
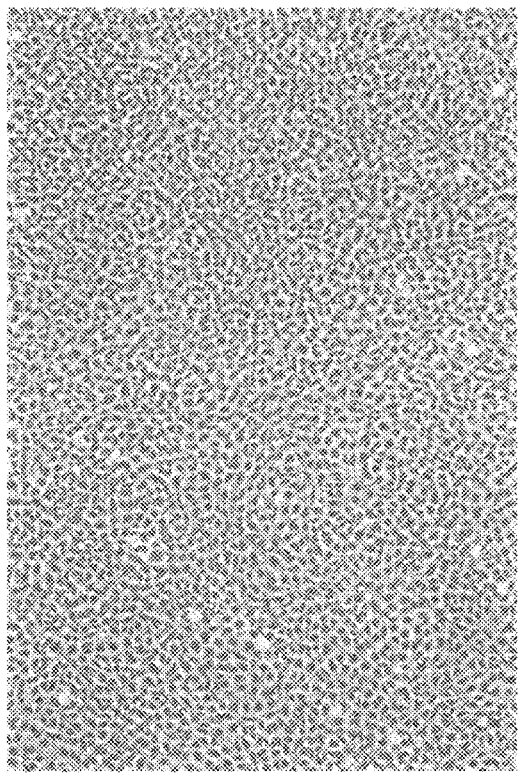
FIG. 8 is a photograph showing the culture experiment in Example 33.

Culture was performed for 4 days and adhesion of cells was observed under microscope (FIG. 8). Attachment of confluent cells to the culture surface was confirmed.

The culture substrate on which cells were cultured was then allowed to stand at 20° C. After 15 minutes, the condition of the cells was observed. The attachment of the cells to the culture surface was confirmed to be maintained.

Figure 9:
FIG. 9 is a photograph showing the culture experiment in Example 33.

The culture substrate on which cells were cultured was then allowed to stand at 5° C. After 15 minutes, the condition of the cells was observed (FIG. 9). Detachment of the cells in the form of a sheet from the culture surface was confirmed.

4. Examples 34 to 36 and Comparative Examples 5 to 7

Samples were prepared in the same manner as above except that NIPAM/C2-SFA (=90/10 mol), NIPAM/C6-SFA (=98/2 mol), and NIPAM/C6-SFA (=96/4 mol) were used in place of the NIPAM/C2-SFA (=95/5 mol) copolymer of Example 33 to prepare samples of Examples 34 to 36; and NIPAM/BMA (=95/5 mol), NIPAM/BMA (=90/10 mol), and an NIPAM homopolymer were used in place of the NIPAM/C2-SFA (=95/5 mol) copolymer of Example 33 to prepare samples of Comparative Examples 5 to 7. The samples were tested in the same manner, except that the polymer to be treated was changed. Table 7 shows the results.

The results confirmed that when using dishes surface-treated with one of the NIPAM/fluorine monomer copolymers of Examples 33 to 36 having an LCST of 15° C. or lower, the cell sheet was not detached at 20° C., but at 5° C. In contrast, when using the polymers of Comparative Examples 5 to 7, the cell sheet was detached when cooling to 20° C., which is room temperature. Cell culture requires various operations, and most of the operations are performed at room temperature. Accordingly, it is a great industrial advantage that cells cultured on the temperature-responsive substrate do not detach during operations at room temperature.

5. Example 37

An AB-type diblock copolymer of NIPAM and C2-SFA [P(NIPAM-block-C2-SFA)] was prepared in the following manner.

(1) Preparation of Poly(N-Isopropylacrylamide) (P(NIPAM))

A polymerization tube was purged with nitrogen and equipped with a stirring bar, and 29.7 mg (0.300 mmol) of copper(I) chloride (hereinafter referred to as CuCl) and 93.7 mg (0.600 mmol) of 2,2'-bipyridyl (hereinafter referred to as bpy) were placed therein. After purging with nitrogen, 8.49 g (75.0 mmol) of NIPAM and 21.5 g of IPA were added, the mixture was frozen and degassed. As a polymerization initiator, 58.5 mg (0.300 mmol) of ethyl α-bromoisobutyrate was added, and the resulting mixture was frozen and degassed. The mixture was then stirred at 25° C. in a nitrogen atmosphere.

After 6 hours, the reaction mixture was added to a large amount of 50° C. water to obtain a white solid. The temperature of the solution containing the solid was set to 20° C. to dissolve the white solid. The resulting solution was passed through an alumina column to remove CuCl and bpy. The solvent was distilled off until the liquid reached an appropriate amount. The liquid was freeze-dried to obtain a white solid again.

The molecular weight of the obtained polymer (white solid) was measured by 1H-NMR (number average) and GPC (weight average). The obtained polymer was confirmed to be P(NIPAM) having a number average molecular weight of 22,600, a weight average molecular weight of 28,300, and a molecular weight distribution of 1.25. 1H-NMR was performed using $CDCl_3$ as a measurement solvent. The GPC measurement was performed using tetrahydrofuran as an eluent and using polymethyl methacrylate as a standard polymer.

(2) Preparation of P(NIPAM-Block-C2-SFA)

19.8 mg (0.200 mmol) of CuCl and 62.4 mg (0.400 mmol) of bpy were placed in a polymerization tube. After purging with nitrogen, 8.16 g (40.0 mmol) of C2-SFA and 17.5 g of IPA were added, and the mixture was frozen and degassed. Then, 4.46 g (0.200 mmol) of the P(NIPAM) prepared above was added, and the mixture was frozen and degassed. The resulting mixture was stirred at 70° C. in a nitrogen atmosphere.

After 6 hours, the reaction mixture was added to a mixed solvent of a large amount of 50° C. water and methanol (water:methanol=1:1 (w/w)) to obtain a white solid. The white solid was dissolved in a mixed solution of IPA and Novec 7200 (fluorinated solvent, produced by Sumitomo 3M Limited, hereinafter referred to as "HFE7200") (IPA: HFE 7200=1:1 (w/w)) and passed through an alumina column to remove CuCl and bpy. After distilling off the solvent, the resulting product was freeze-dried with benzene to obtain a white solid again.

The obtained polymer (white solid) was evaluated by 1H-NMR and GPC. The polymer was confirmed to be P(NIPAM-block-C2-SFA) having a number average molecular weight of 52,800, a weight average molecular weight of 78,100, and a molecular weight distribution of 1.48.

(3) Test Method

A test was performed in the same manner as in Example 33 except that P(NIPAM-block-C2-)SFA was used in place of the NIPAM/C2-SFA (=95/5 mol) copolymer, and no irradiation with an electron beam was performed. Table 7 shows the results. The results show that block copolymerization of NIPAM and C2-SFA can immobilize a polymer on the substrate surface without electron beam irradiation.

6. Example 38

An ABA-type triblock copolymer of NIPAM and C2-SFA (P(NIPAM-block-C2-SFA-block-NIPAM)) was prepared in the following manner.

(1) Preparation of P(NIPAM)

Polymerization was performed in the same manner as in Example 37 (1) to obtain P(NIPAM) with a number average molecular weight of 24,300, a weight average molecular weight of 29,700, and a molecular weight distribution of 1.22.

(2) Preparation of P(NIPAM-Block-C2-SFA)

Polymerization was performed in the same manner as in Example 37(2), except that 4.86 g of P(NIPAM) was added in place of 4.46 g of P(NIPAM). As a result, P(NIPAMblock-C2-SFA) with a number average molecular weight of 51,500, a weight average molecular weight of 80,400, and a molecular weight distribution of 1.56, was obtained.

(3) Preparation of P(NIPAM-Block-C2-SFA-Block-NIPAM)

9.90 mg (0.100 mmol) of CuCl and 31.2 mg (0.200 mmol) of bpy were placed into a polymerization tube. After purging with nitrogen, 3.39 g (30.0 mmol) of NIPAM and 21.5 g of IPA were added. After the mixture was frozen and degassed, 5.15 g (0.100 mmol) of P(NIPAM-block-C2-SFA) prepared above in Example 37 (2) was added. After the mixture was frozen and degassed, the resulting mixture was stirred at 70° C. in a nitrogen atmosphere.

After 6 hours, the reaction mixture was added to a mixed solvent of a large amount of 50° C. water and methanol (water:methanol=1:1 (w/w)) to obtain a white solid. The white solid was then dissolved in a mixed solution of IPA and HFE7200 (IPA:HFE 7200=1:1 (w/w)), and the solution was passed through an alumina column to remove CuCl and bpy. After the solvent was distilled off, the resulting product was freeze-dried with benzene to obtain a white solid again.

The white solid was evaluated by 1H-NMR and GPC. The white solid was confirmed to be P(NIPAM-block-C2-SFA-block-NIPAM) with a number average molecular weight of 82,900, a weight average molecular weight of 115,000, and a molecular weight distribution of 1.39.

(4) Test Method

A test was performed in the same manner except that P(NIPAM-block-C2-SFA-block-NIPAM) was used in place of the NIPAM/C2-SFA (=95/5 mol) copolymer of Example 33, and no irradiation with an electron beam was performed. Table 7 shows the results. The results show that block copolymerization of NIPAM and C2-SFA can immobilize the polymer on the substrate surface without electron beam irradiation.

TABLE 7

| | | | | | Spin-coated film of the solution polymerization polymer | | | | | | |
|---|---|---|---|---|---|---|---|---|---|---|---|
| | Polymer | | | Irradiation | | | | | | | |
| | | Composition ratio | Fluorine content | of electron beam | Contact angle (°) | | | | | LSCT | Presence of intermediate |
| Example | Type | (mol/mol) | (wt. %) | (200 kGy) | 5° C. | 20° C. | 40° C. | $\theta_{5 \to 40° C.}$ | $\theta_{20 \to 40° C.}$ | (° C.) | water |
| Example 33 | P(NIPAM/C2-SFA) | 95/5 | 3.8 | Yes | 9 | 38 | 56 | 47 | — | 13 | Yes |
| Example 34 | | 90/10 | 7.7 | | 13 | 41 | 65 | 52 | — | 8 | Yes |
| Example 35 | P(NIPAM/C6-SFA) | 98/2 | 4.2 | | 12 | 50 | 57 | 45 | — | 12 | Yes |
| Example 36 | | 96/4 | 7.9 | | 15 | 55 | 62 | 47 | — | 8 | Yes |
| Example 37 | P(NIPAM-block-C2-SFA) | 1/1 | 29.5 | No | 9 | 14 | 51 | — | 37 | 31 | Yes |
| Example 38 | P(NIPAM-block-C2-SFA-block-NIPAM) | 1/1/1 | 22.4 | | 7 | 9 | 50 | — | 41 | 32 | Yes |
| Comparative Example 5 | P(NIPAM/BMA) | 95/5 | 0 | Yes | 8 | 10 | 45 | — | 35 | 21 | Yes |
| Comparative Example 6 | | 90/10 | 0 | | 9 | 12 | 48 | — | 36 | 17 | Yes |
| Comparative Example 7 | PNIPAM | 100/0 | 0 | | 6 | 7 | 47 | — | 40 | 32 | Yes |

| | Cell attachment and detachment | | | | | |
|---|---|---|---|---|---|---|
| | After 1 day | | | After 4 days | | |
| Example | 37° C. after 1 day | → 20° C. cooling, after 15 minutes | → 5° C. cooling, after 15 minutes | 37° C. after 1 day | → 20° C. cooling, after 15 minutes | → 5° C. cooling, after 15 minutes |
| Example 33 | Attached | Attached | Detached | Confluent | Confluent | Detached |
| Example 34 | Attached | Attached | Detached | Confluent | Confluent | Detached |
| Example 35 | Attached | Attached | Detached | Confluent | Confluent | Detached |
| Example 36 | Attached | Attached | Detached | Confluent | Confluent | Detached |
| Example 37 | Attached | Detached | Detached | Confluent | Detached | Detached |
| Example 38 | Attached | Detached | Detached | Confluent | Detached | Detached |
| Comparative Example 5 | Attached | Detached | Detached | Confluent | Detached | Detached |
| Comparative Example 6 | Attached | Detached | Detached | Confluent | Detached | Detached |
| Comparative Example 7 | Attached | Detached | Detached | Confluent | Detached | Detached |

(Common experimental conditions)
Solvent for diluting polymer: isopropyl alcohol
Polymer concentration: $1 \times 10^{-4}$ wt. %
Amount of monomer solution applied to a 3.5-cm dish (Falcon 3001): 0.5 mL

The invention claimed is:

1. A temperature-responsive substrate having on its surface a layer comprising a blend polymer, at least one polymer constituting the blend polymer is responsive to temperature, and at least one polymer constituting the blend polymer comprises a fluorine-containing monomer-derived unit, wherein said temperature-responsive substrate is a cell culture substrate, wherein the fluorine-containing monomer is represented by formula (1):

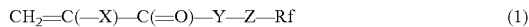

wherein X is hydrogen, a $C_{1-21}$ linear or branched alkyl group, fluorine, chlorine, bromine, iodine, $CFX^1X^2$—(wherein $X^1$ and $X^2$ are hydrogen, fluorine, chlorine, bromine, or iodine), cyano, a $C_{1-21}$ linear or branched fluoroalkyl group, a substituted or unsubstituted benzyl group, or a substituted or unsubstituted phenyl group;

Y is —O— or —NH—;

Z is a $C_{1-10}$ aliphatic group, a $C_{6-10}$ aromatic group, or a $C_{6-10}$ cyclic aliphatic group, —$CH_2CH_2N(R^1)SO_2$— wherein $R^1$ is a $C_{1-4}$ alkyl group, —$CH_2CH(OZ)^1)CH_2$— wherein $Z^1$ is hydrogen or acetyl, —$(CH_2)_m$—$SO_2$—$(CH_2)_n$—, —$(CH_2)_m$—S—$(CH_2)_n$— wherein m is 1 to 10, and n is 0 to 10, or —$(CH_2)_m$—COO— wherein m is 1 to 10:

Rf is a $C_{1-20}$ linear or branched fluoroalkyl group optionally containing a heteroatom, and wherein the blend polymer comprises at least one polymer comprising a fluorine-containing monomer-derived unit in an amount of at least 5 mol %, based on the sum of all monomer units, and at least one temperature-responsive polymer comprising a fluorine-containing monomer-derived unit in an amount of 0 to 1 mol %, based on the sum of all monomer units.

2. The temperature-responsive substrate according to claim 1, wherein at least one temperature-responsive polymer constituting the blend polymer has a lower critical solution temperature (LCST) of 0 to 15° C.

3. The temperature-responsive substrate according to claim 1, wherein the at least one polymer comprising a fluorine-containing monomer-derived unit in an amount of at least 5 mol % based on the sum of all monomer units contains fluorine in an amount of 2 to 40 wt. %, based on the weight of the polymer.

4. The temperature-responsive substrate according to claim 1, wherein the fluorine-containing monomer contains a fluoroalkyl group.

5. The temperature-responsive substrate according to claim 1, wherein Rf in the fluorine-containing monomer represented by formula (1) is a $C_{1-6}$ linear or branched fluoroalkyl group optionally containing a heteroatom.

6. The temperature-responsive substrate according to claim 1, wherein said at least one polymer comprising a fluorine-containing monomer-derived unit in an amount of at least 5 mol %, based on the sum of all monomer units is a temperature-responsive polymer.

7. The temperature-responsive substrate according to claim 1, wherein the proportion of the fluorine-containing monomer-derived unit is 0.5 to 10 mol %, based on the sum of all monomer units constituting the blend polymer.

8. A method for detaching cells from a culture substrate, which comprises providing the temperature-responsive substrate according to claim 1, detaching the cells, which are cultured on the surface of the temperature-responsive substrate, from the surface in a temperature environment lower than that of the LCST of at least one temperature-responsive polymer constituting the blend polymer.

9. The method according to claim 8, wherein the LCST of at least one temperature-responsive polymer constituting the blend polymer is 0 to 15° C.

10. The method according to claim 9, wherein the at least one polymer comprising a fluorine-containing monomer-derived unit in an amount of at least 5 mol % based on the sum of all monomer units is a temperature-responsive polymer containing fluorine in an amount of 2 to 20 wt. %, based on the weight of the polymer.

11. A method for producing a cell sheet, which comprises providing the temperature-responsive substrate according to claim 1, detaching a sheet of cells, which are cultured on the surface of the temperature-responsive substrate, from the surface in a temperature environment lower than that of the LCST of at least one temperature-responsive polymer constituting the blend polymer.

12. The method according to claim 11, wherein at last one temperature-responsive polymer constituting the blend polymer has an LCST of 0 to 15° C.

13. The method according to claim 12, wherein the at least one polymer comprising a fluorine-containing monomer-derived unit in an amount of at least 5 mol % based on the sum of all monomer units is a temperature-responsive polymer containing 2 to 20 wt. % of fluorine, based on the weight of the polymer.

* * * * *